United States Patent
Tariyal et al.

(10) Patent No.: US 9,918,702 B2
(45) Date of Patent: Mar. 20, 2018

(54) SYSTEM AND METHOD FOR MONITORING HEALTH BASED ON COLLECTED BODILY FLUID

(71) Applicant: NEXTGEN JANE, INC., Oakland, CA (US)

(72) Inventors: Ridhi Tariyal, Cambridge, MA (US); Stephen Gire, Cambridge, MA (US)

(73) Assignee: NextGen Jane, Inc., Oakland, CA (US)

( * ) Notice: Subject to any disclaimer, the term of this patent is extended or adjusted under 35 U.S.C. 154(b) by 0 days.

(21) Appl. No.: 15/203,464

(22) Filed: Jul. 6, 2016

(65) Prior Publication Data
US 2016/0324506 A1  Nov. 10, 2016

Related U.S. Application Data

(63) Continuation of application No. PCT/US2015/044312, filed on Aug. 7, 2015.
(Continued)

(51) Int. Cl.
*A61B 5/00* (2006.01)
*A61B 10/00* (2006.01)
(Continued)

(52) U.S. Cl.
CPC .......... *A61B 10/0045* (2013.01); *A61B 5/157* (2013.01); *A61B 5/150358* (2013.01);
(Continued)

(58) Field of Classification Search
CPC ................ A61B 10/0045; A61B 10/02; A61B 2010/0061
(Continued)

(56) References Cited

U.S. PATENT DOCUMENTS

| 4,257,427 A | 3/1981 | Bucalo |
| 4,675,286 A | 6/1987 | Calenoff |

(Continued)

FOREIGN PATENT DOCUMENTS

| EP | 1148819 B1 | 10/2010 |
| WO | WO-9855159 A2 | 12/1998 |

(Continued)

OTHER PUBLICATIONS

Tjiong, et al., Increased IL-6 and IL-8 levels in cervicovaginal secretions of patients with cervical cancer. Gynecol Oncol. May 1999;73(2):285-91.
(Continued)

*Primary Examiner* — Daniel Cerioni
(74) *Attorney, Agent, or Firm* — Wilson, Sonsini, Goodrich & Rosati

(57) ABSTRACT

A medical kit for analysis of vaginal biological samples includes a sample collector, an extractor, and an assay cartridge. The sample collector is compressible and insertable in a vaginal canal for collecting biological samples, and includes a cup-shaped head configured to cradle a cervical os. The extractor includes a sample receptacle configured to receive the sample collector via an open end. The extractor includes a compression mechanism with a compression element that is movable inwards into the open end of the sample receptacle to apply a compression force in response to activation of a release element. The extractor further includes a reservoir in fluid communication with the sample receptacle, the reservoir receiving the biological samples from the sample collector in response to the compression force being applied within the sample receptacle. The assay cartridge has a docking mechanism configured to fluidly communicate with the reservoir of the extractor.

29 Claims, 13 Drawing Sheets

Related U.S. Application Data

(60) Provisional application No. 62/036,469, filed on Aug. 12, 2014, provisional application No. 62/132,394, filed on Mar. 12, 2015.

(51) Int. Cl.

| | | |
|---|---|---|
| *A61B 10/02* | (2006.01) | |
| *A61B 5/15* | (2006.01) | |
| *A61B 5/157* | (2006.01) | |
| *A61F 13/20* | (2006.01) | |
| *A61F 13/472* | (2006.01) | |
| *A61M 1/00* | (2006.01) | |
| *A61M 39/24* | (2006.01) | |

(52) U.S. Cl.
CPC ...... *A61B 5/150755* (2013.01); *A61B 5/4362* (2013.01); *A61B 5/7282* (2013.01); *A61B 10/0058* (2013.01); *A61B 10/0096* (2013.01); *A61B 10/0291* (2013.01); *A61F 13/2045* (2013.01); *A61F 13/472* (2013.01); *A61M 1/0056* (2013.01); *A61M 39/24* (2013.01); *A61B 2010/008* (2013.01); *A61B 2010/0074* (2013.01); *A61B 2010/0208* (2013.01); *A61B 2010/0216* (2013.01)

(58) Field of Classification Search
USPC .................................................. 600/573, 582
See application file for complete search history.

(56) References Cited

U.S. PATENT DOCUMENTS

| | | | |
|---|---|---|---|
| 5,725,481 A | 3/1998 | Buck et al. | |
| 5,750,341 A | 5/1998 | MacEvicz | |
| 5,830,199 A | 11/1998 | Chaffringeon | |
| 5,843,575 A | 12/1998 | Wang et al. | |
| 5,856,174 A | 1/1999 | Lipshutz et al. | |
| 5,858,535 A | 1/1999 | Wang et al. | |
| 5,891,126 A | 4/1999 | Osborn, III et al. | |
| 6,007,498 A | 12/1999 | Buck et al. | |
| 6,126,616 A | 10/2000 | Sanyal | |
| 6,174,293 B1 | 1/2001 | Buck et al. | |
| 6,206,839 B1 | 3/2001 | Zwelling-Aamot | |
| 6,306,597 B1 | 10/2001 | MacEvicz | |
| 6,409,713 B1 | 6/2002 | Osborn, III et al. | |
| 6,479,727 B1 | 11/2002 | Roe | |
| 6,531,435 B1 | 3/2003 | Resheski-Wedepohl et al. | |
| 6,649,359 B2 | 11/2003 | Mutter et al. | |
| 6,656,913 B1 | 12/2003 | Resheski-Wedepohl et al. | |
| 6,664,104 B2 | 12/2003 | Pourahmadi et al. | |
| 6,702,759 B2 | 3/2004 | Pevoto | |
| 6,811,549 B2 | 11/2004 | Fleming | |
| 6,888,043 B2 | 5/2005 | Geiser et al. | |
| 6,890,325 B2 | 5/2005 | Edens et al. | |
| 6,899,700 B2 | 5/2005 | Gehling et al. | |
| 6,936,013 B2 | 8/2005 | Pevoto | |
| 7,056,891 B2 | 6/2006 | Resheski-Wedepohl et al. | |
| 7,115,116 B2 | 10/2006 | Hlaban et al. | |
| 7,115,400 B1 | 10/2006 | Adessi et al. | |
| 7,128,877 B2 | 10/2006 | Quay et al. | |
| 7,183,381 B2 | 2/2007 | Varadhachary et al. | |
| 7,211,390 B2 | 5/2007 | Rothberg et al. | |
| 7,232,656 B2 | 6/2007 | Balasubramanian et al. | |
| 7,244,559 B2 | 7/2007 | Rothberg et al. | |
| 7,264,929 B2 | 9/2007 | Rothberg et al. | |
| 7,291,477 B2 | 11/2007 | Alderete et al. | |
| 7,314,453 B2 | 1/2008 | Kuo | |
| 7,323,305 B2 | 1/2008 | Leamon et al. | |
| 7,420,033 B2 | 9/2008 | Varadhachary et al. | |
| 7,638,099 B2 | 12/2009 | Lloyd, Jr. et al. | |
| 7,648,829 B2 | 1/2010 | Alderete et al. | |
| 7,776,525 B2 | 8/2010 | Kuroda et al. | |
| 7,803,567 B2 | 9/2010 | Alderete et al. | |
| 7,935,860 B2 | 5/2011 | Dodge et al. | |
| 7,943,294 B2 | 5/2011 | Hussa et al. | |
| 7,948,015 B2 | 5/2011 | Rothberg et al. | |
| 7,994,387 B2 | 8/2011 | Minoguchi et al. | |
| 8,241,086 B2 | 8/2012 | Kim | |
| 8,372,581 B2 | 2/2013 | Hussa et al. | |
| 8,398,606 B2 | 3/2013 | Fleming | |
| 8,641,642 B2 | 2/2014 | Giddings et al. | |
| 8,685,748 B2 | 4/2014 | Lloyd et al. | |
| 8,722,349 B2 | 5/2014 | Goldman | |
| 8,852,872 B2 | 10/2014 | Hussa et al. | |
| 8,911,988 B2 | 12/2014 | Miller | |
| 9,060,753 B2 | 6/2015 | Lundkvist et al. | |
| 9,078,642 B2 | 7/2015 | Vom et al. | |
| 9,144,420 B2 | 9/2015 | Zavala | |
| 9,168,028 B2 | 10/2015 | Shany et al. | |
| 9,417,210 B2 | 8/2016 | Arlen et al. | |
| 2002/0072702 A1* | 6/2002 | Quay ................ A61B 5/14546 604/74 | |
| 2002/0169433 A1 | 11/2002 | Osborn et al. | |
| 2003/0045829 A1 | 3/2003 | Gehling et al. | |
| 2003/0073147 A1 | 4/2003 | Alderete et al. | |
| 2003/0113746 A1 | 6/2003 | Leyendecker | |
| 2003/0120180 A1 | 6/2003 | Kaylor et al. | |
| 2003/0120224 A1 | 6/2003 | Geiser et al. | |
| 2003/0120225 A1 | 6/2003 | Everhart et al. | |
| 2004/0053856 A1 | 3/2004 | Resheski-Wedepohl et al. | |
| 2004/0078230 A1 | 4/2004 | Karas | |
| 2004/0121379 A1 | 6/2004 | Ohan | |
| 2004/0266025 A1 | 12/2004 | Hickok et al. | |
| 2005/0020937 A1 | 1/2005 | Reed et al. | |
| 2005/0020993 A1 | 1/2005 | Fleming | |
| 2005/0124003 A1 | 6/2005 | Atala et al. | |
| 2005/0187507 A1 | 8/2005 | Reed et al. | |
| 2005/0276836 A1 | 12/2005 | Wilson et al. | |
| 2006/0024725 A1 | 2/2006 | Hussa et al. | |
| 2006/0024757 A1 | 2/2006 | Hussa et al. | |
| 2006/0036138 A1 | 2/2006 | Heller et al. | |
| 2006/0287611 A1 | 12/2006 | Fleming | |
| 2007/0231358 A1 | 10/2007 | Ebmeier et al. | |
| 2008/0113358 A1 | 5/2008 | Kapur et al. | |
| 2008/0160580 A1 | 7/2008 | Adessi et al. | |
| 2008/0217246 A1 | 9/2008 | Benn et al. | |
| 2008/0286795 A1 | 11/2008 | Kawashima et al. | |
| 2008/0299543 A1 | 12/2008 | Gailer | |
| 2009/0011417 A1* | 1/2009 | Maltezos ................ B01L 3/502 435/6.14 | |
| 2009/0043224 A1 | 2/2009 | Lundkvist et al. | |
| 2009/0104650 A1 | 4/2009 | Walton et al. | |
| 2009/0105678 A1 | 4/2009 | Minoguchi et al. | |
| 2009/0148933 A1 | 6/2009 | Battrell et al. | |
| 2009/0156965 A1 | 6/2009 | Fleming | |
| 2009/0227930 A1 | 9/2009 | Crisp | |
| 2009/0246750 A1 | 10/2009 | Lloyd et al. | |
| 2010/0030189 A1 | 2/2010 | Fleming | |
| 2010/0035349 A1 | 2/2010 | Bau et al. | |
| 2010/0086948 A1 | 4/2010 | Gold et al. | |
| 2010/0184046 A1 | 7/2010 | Klass et al. | |
| 2010/0216131 A1 | 8/2010 | Luthra et al. | |
| 2010/0221752 A2 | 9/2010 | Gold et al. | |
| 2010/0267003 A1 | 10/2010 | Goldman | |
| 2010/0274155 A1* | 10/2010 | Battrell ............ A61B 10/0096 600/572 | |
| 2010/0296087 A1 | 11/2010 | Gailer | |
| 2011/0027795 A1 | 2/2011 | Mantzaris et al. | |
| 2011/0086378 A1 | 4/2011 | Shany et al. | |
| 2011/0111386 A1* | 5/2011 | Rogers ............ A61B 10/0045 435/5 | |
| 2011/0166432 A1 | 7/2011 | Fleming | |
| 2011/0192239 A1 | 8/2011 | Selinfreund et al. | |
| 2011/0195488 A1 | 8/2011 | Selinfreund et al. | |
| 2011/0207621 A1 | 8/2011 | Montagu et al. | |
| 2012/0122726 A1 | 5/2012 | Posada et al. | |
| 2012/0149017 A1 | 6/2012 | Tabibzadeh et al. | |
| 2012/0165217 A1 | 6/2012 | Gold et al. | |
| 2012/0310113 A1 | 12/2012 | Giddings et al. | |
| 2012/0316409 A1 | 12/2012 | Crisp | |
| 2013/0085680 A1 | 4/2013 | Arlen et al. | |
| 2013/0252245 A1 | 9/2013 | Micallef et al. | |
| 2013/0331298 A1 | 12/2013 | Rea | |

(56) References Cited

U.S. PATENT DOCUMENTS

| | | | |
|---|---|---|---|
| 2013/0337439 | A1 | 12/2013 | Goncalves Pereira Nobre et al. |
| 2013/0344588 | A1 | 12/2013 | Halushka et al. |
| 2014/0066807 | A1 | 3/2014 | Lundkvist et al. |
| 2014/0099649 | A1 | 4/2014 | Mitsuhashi |
| 2014/0128345 | A1 | 5/2014 | Woodrow et al. |
| 2014/0134246 | A1 | 5/2014 | Venkatesh et al. |
| 2014/0309606 | A1 | 10/2014 | Richlen et al. |
| 2015/0044708 | A1 | 2/2015 | Hussa et al. |
| 2015/0087935 | A1 | 3/2015 | Davis et al. |
| 2015/0185184 | A1 | 7/2015 | Guia et al. |
| 2015/0217019 | A1 | 8/2015 | Martello |
| 2015/0283284 | A1 | 10/2015 | Azad et al. |
| 2015/0342577 | A1 | 12/2015 | Fleming et al. |
| 2016/0011225 | A1 | 1/2016 | Holmes |
| 2016/0143631 | A1 | 5/2016 | Zavala |

FOREIGN PATENT DOCUMENTS

| | | | |
|---|---|---|---|
| WO | WO-0055173 | A1 | 9/2000 |
| WO | WO-0170804 | A1 | 9/2001 |
| WO | WO-0248820 | A2 | 6/2002 |
| WO | WO-02095060 | A2 | 11/2002 |
| WO | WO-03011144 | A1 | 2/2003 |
| WO | WO-03020240 | A2 | 3/2003 |
| WO | WO-0305695 | A1 | 7/2003 |
| WO | WO-03057264 | A1 | 7/2003 |
| WO | WO-03057305 | A1 | 7/2003 |
| WO | WO-0248820 | A3 | 8/2004 |
| WO | WO-2004071304 | A1 | 8/2004 |
| WO | WO-2004071427 | A2 | 8/2004 |
| WO | WO-2005102526 | A1 | 11/2005 |
| WO | WO-2006017341 | A2 | 2/2006 |
| WO | WO-2006017746 | A2 | 2/2006 |
| WO | WO-2006083853 | A2 | 8/2006 |
| WO | WO-2008112290 | A2 | 9/2008 |
| WO | WO-2009035706 | A1 | 3/2009 |
| WO | WO-2009077876 | A2 | 6/2009 |
| WO | WO-2010042525 | A1 | 4/2010 |
| WO | WO-2010085841 | A1 | 8/2010 |
| WO | WO-2011043840 | A1 | 4/2011 |
| WO | WO-2011127467 | A1 | 10/2011 |
| WO | WO-2012078308 | A1 | 6/2012 |
| WO | WO-2012151237 | A1 | 11/2012 |
| WO | WO-2014015192 | A1 | 1/2014 |
| WO | WO-2015050875 | A1 | 4/2015 |
| WO | WO-2015059686 | A1 | 4/2015 |
| WO | WO-2015066750 | A1 | 5/2015 |
| WO | WO-2016025726 | A1 | 2/2016 |
| WO | WO-2016028497 | A1 | 2/2016 |
| WO | WO-2016033287 | A1 | 3/2016 |
| WO | WO-2016033646 | A1 | 3/2016 |
| WO | WO-2016094409 | A1 | 6/2016 |

OTHER PUBLICATIONS

Bulletti, et al. Endometriosis and infertility. J Assist Reprod Genet. Aug. 2010;27(8):441-7. doi: 10.1007/s10815-010-9436-1. Epub Jun. 25, 2010.

Campbell, et al. Evaluation of the OSOM Trichomonas rapid test versus wet preparation examination for detection of Trichomonas vaginalis vaginitis in specimens from women with a low prevalence of infection. J Clin Microbiol. Oct. 2008;46(10):3467-9. doi: 10.1128/JCM.00671-08. Epub Aug. 6, 2008.

Chang, et al. Effect of iron deficiency anemia in pregnancy on child mental development in rural China. Pediatrics. Mar. 2013;131(3):e755-63. doi: 10.1542/peds.2011-3513. Epub Feb. 11, 2013.

Chudecka-Glaz, et al. Serum HE4, CA125, YKL-40, bcl-2, cathepsin-L and prediction optimal debulking surgery, response to chemotherapy in ovarian cancer. J Ovarian Res. Jun. 10, 2014;7:62. doi: 10.1186/1757-2215-7-62. eCollection 2014.

Da Fonseca, et al. Prophylactic administration of progesterone by vaginal suppository to reduce the incidence of spontaneous preterm birth in women at increased risk: a randomized placebo-controlled double-blind study. Am J Obstet Gynecol. Feb. 2003;188(2):419-24.

Deguchi, et al. Emergence and spread of drug resistant Neisseria gonorrhoeae. J Urol. Sep. 2010;184(3):851-8; quiz 1235. doi: 10.1016/j.juro.2010.04.078.

Di Quinzio, et al. Proteomic analysis and characterisation of human cervico-vaginal fluid proteins. Aust N Z J Obstet Gynaecol. Feb. 2007;47(1):9-15.

Eschenbach. History and review of bacterial vaginosis. Am J Obstet Gynecol. Aug. 1993;169(2 Pt 2):441-5.

Gaydos, et al. Comparison of three nucleic acid amplification tests for detection of Chlamydia trachomatis in urine specimens. J Clin Microbiol. Jul. 2004;42(7):3041-5.

Hale, et al. Hormonal changes and biomarkers in late reproductive age, menopausal transition and menopause. Best Pract Res Clin Obstet Gynaecol. Feb. 2009;23(1):7-23. doi: 10.1016/j.bpobgyn. 2008.10.001. Epub Dec. 1, 2008.

Imudia, et al. Transcervical retrieval of fetal cells in the practice of modern medicine: a review of the current literature and future direction. Fertil Steril. Apr. 2010;93(6):1725-30. doi: 10.1016/j. fertnstert.2009.11.022. Epub Jan. 13, 2010.

International search report and written opinion dated Nov. 4, 2015 for PCT/US2015/044312.

Jashnani, et al. Alfa-fetoprotein secreting ovarian sex cord-stromal tumor. Indian J Pathol Microbiol. Jan.-Mar. 2013;56(1):54-6. doi: 10.4103/0377-4929.116152.

Javors, et al. Current status of carbohydrate deficient transferrin, total serum sialic acid, sialic acid index of apolipoprotein J and serum beta-hexosaminidase as markers for alcohol consumption. Addiction. Dec. 2003;98 Suppl 2:45-50.

Kaastrup, et al. Polymerization-based signal amplification under ambient conditions with thirty-five second reaction times. Lab Chip. Oct. 21, 2012;12(20):4055-8.

Kumar, et al. Robbins Basic Pathology ((8th ed.) ed.). Saunders Elsevier. pp. 718-721. May 24, 2007.

Leitich, et al. Cervicovaginal fetal fibronectin as a marker for preterm delivery: a meta-analysis. Am J Obstet Gynecol. May 1999;180(5):1169-76.

Lin, et al. Relationships between folate and inflammatory features of asthma. J Allergy Clin Immunol. Mar. 2013;131(3):918-20. doi: 10.1016/j.jaci.2012.10.046. Epub Dec. 11, 2012.

Lynge, et al. Cervical cancer screening at crossroads. APMIS. Aug. 2014;122(8):667-73. doi: 10.1111/apm.12279.

Meyers, et al. USPSTF recommendations for STI screening. Am Fam Physician. Mar. 15, 2008;77(6):819-24.

Moran. Gonorrhoea. BMJ Clin Evid. Mar. 1, 2007;2007. pii: 1604.

Mustafa, et al. Risk factors for cervical cancer: diagnosis and management. IOSR Journal of Dental and Medical Sciences. Jun. 2016; 15(6):104-110.

Negro, et al. Increased pregnancy loss rate in thyroid antibody negative women with TSH levels between 2.5 and 5.0 in the first trimester of pregnancy. J Clin Endocrinol Metab. Sep. 2010;95(9):E44-8. doi: 10.1210/jc.2010-0340. Epub Jun. 9, 2010.

Paavonen, et al. Sexually transmitted diseases. Lower genital tract infections in women. Infect Dis Clin North Am. Mar. 1987;1(1):179-98.

Peterson. Biomarkers for alcohol use and abuse—a summary. Alcohol Res Health. 2004-2005;28(1):30-7.

Piek, et al. Ovarian carcinogenesis: an alternative hypothesis. Adv Exp Med Biol. 2008;622:79-87. doi: 10.1007/978-0-387-68969-2_7.

Ratnam. The laboratory diagnosis of syphilis. Can J Infect Dis Med Microbiol. Jan. 2005;16(1):45-51.

Rochester. Bisphenol A and human health: a review of the literature. Reprod Toxicol. Dec. 2013;42:132-55. doi: 10.1016/j.reprotox. 2013.08.008. Epub Aug. 30, 2013.

Sparks. Vaginitis. The Journal of Reproductive Medicine. 1991; 36(10):745-752.

Tabrizi, et al. A self-administered technique for the detection of sexually transmitted diseases in remote communities. J Infect Dis. Jul. 1997;176(1):289-92.

Tal, et al. Characterization of women with elevated antimüllerian hormone levels (AMH): correlation of AMH with polycystic ovar-

(56) References Cited

OTHER PUBLICATIONS ian syndrome phenotypes and assisted reproductive technology outcomes. Am J Obstet Gynecol. Jul. 2014;211(1):59.e1-8. doi: 10.1016/j.ajog.2014.02.026. Epub Mar. 2, 2014.

Verhaegen, et al. Accuracy of single progesterone test to predict early pregnancy outcome in women with pain or bleeding: meta-analysis of cohort studies. BMJ. Sep. 27, 2012;345:e6077. doi: 10.1136/bmj.e6077.

Burney, R.O. et al., MicroRNA expression profiling of eutopic secretory endometrium in women with versus without endometriosis. Molecular Human Reproduction, vol. 15, No. 10 pp. 625-631, Aug. 2009.

Dyson, MT. et al., Genome-Wide DNA Methylation Analysis Predicts an Epigenetic Switch for GATA Factor Expression in Endometriosis. PLOSE Genetics. Mar. 6, 2014. https://doi.org/10.1371/journal.pgen.1004158.

Filigheddu, N. et al., Differential Expression of MicroRNAs between Eutopic and Ectopic Endometrium in Ovarian Endometriosis. Hindawi Publishing Corp. Journal of Biomedicine and Biotechnology. Mar. 2009. vol. 2010, Article ID 369549, 29 pages doi:10.1155/2010/369549.

Hawkins, S.M. et al., Functional MicroRNA involved in endometriosis. Mol Endocrinol. May 2011; 25(5): 821-832.

Koukoura, O. et al., DNA methylation in endometriosis (Review). Molecular Medicine Reports. 2016;13:2939-2949.

Naqvi, H. et al., Altered Genome-Wide Methylation in Endometriosis. Sage Journals Reproductive Sciences. 21(10):Apr. 30, 2014.

Wang, Y. et al., Genome-Wide Microarray Analysis of Long Non-Coding RNAs in Eutopic Secretory Endometrium with Endometriosis. Cellular Physiology and Biochemistry. 2015;37:2213-2245.

* cited by examiner

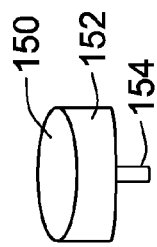
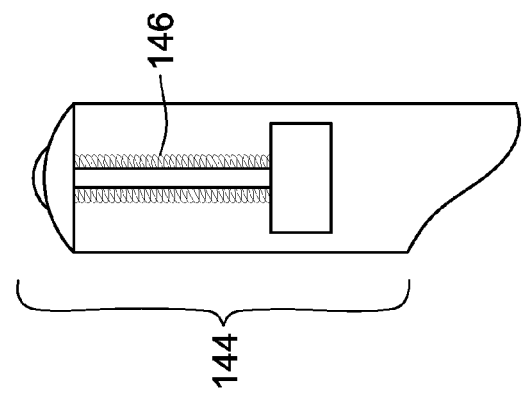
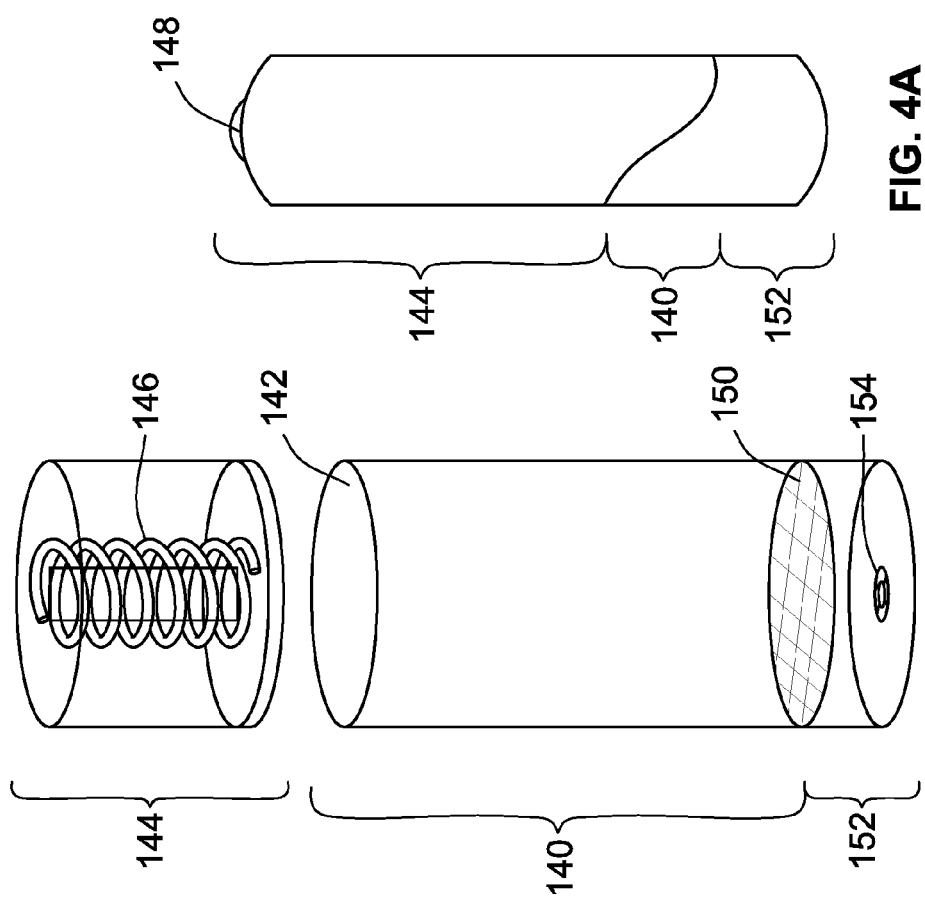

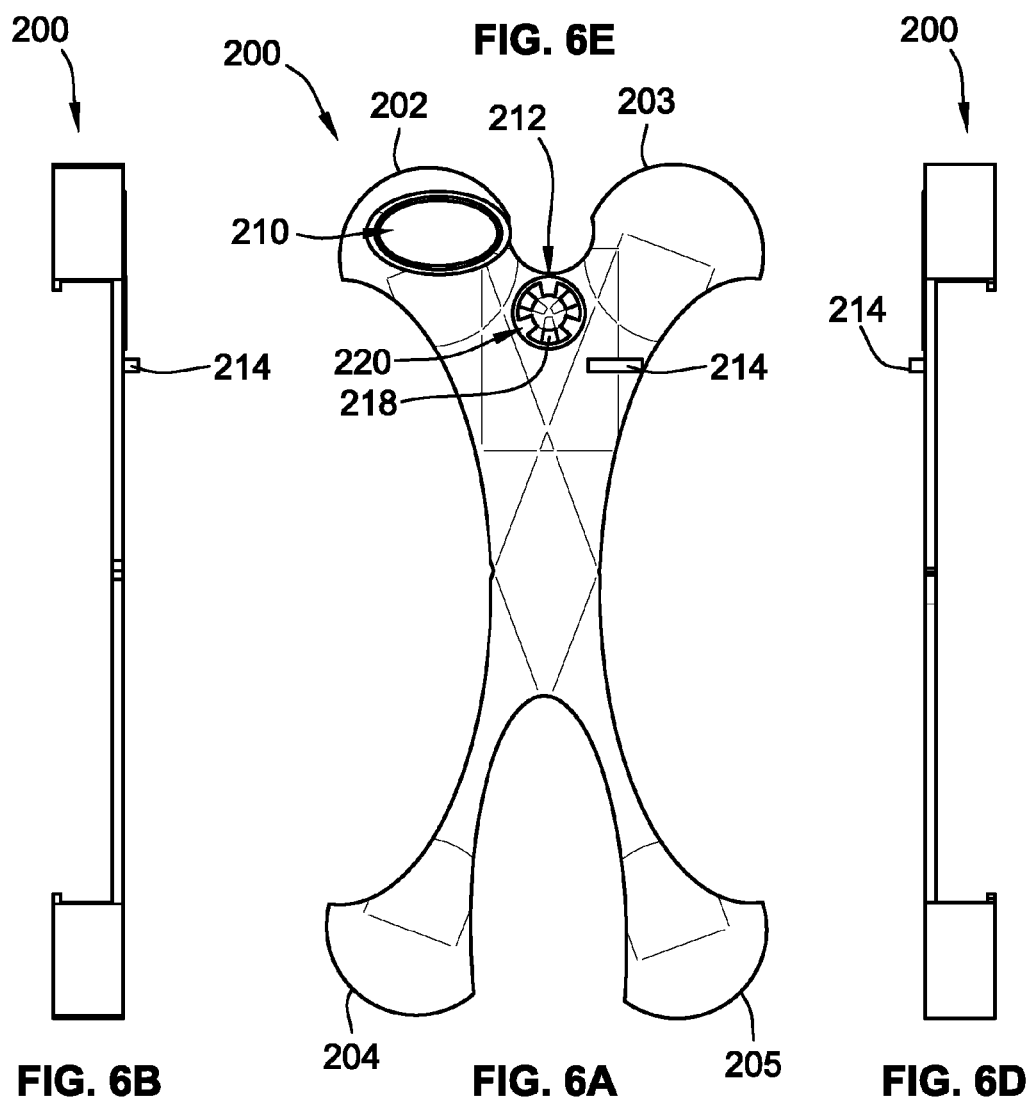

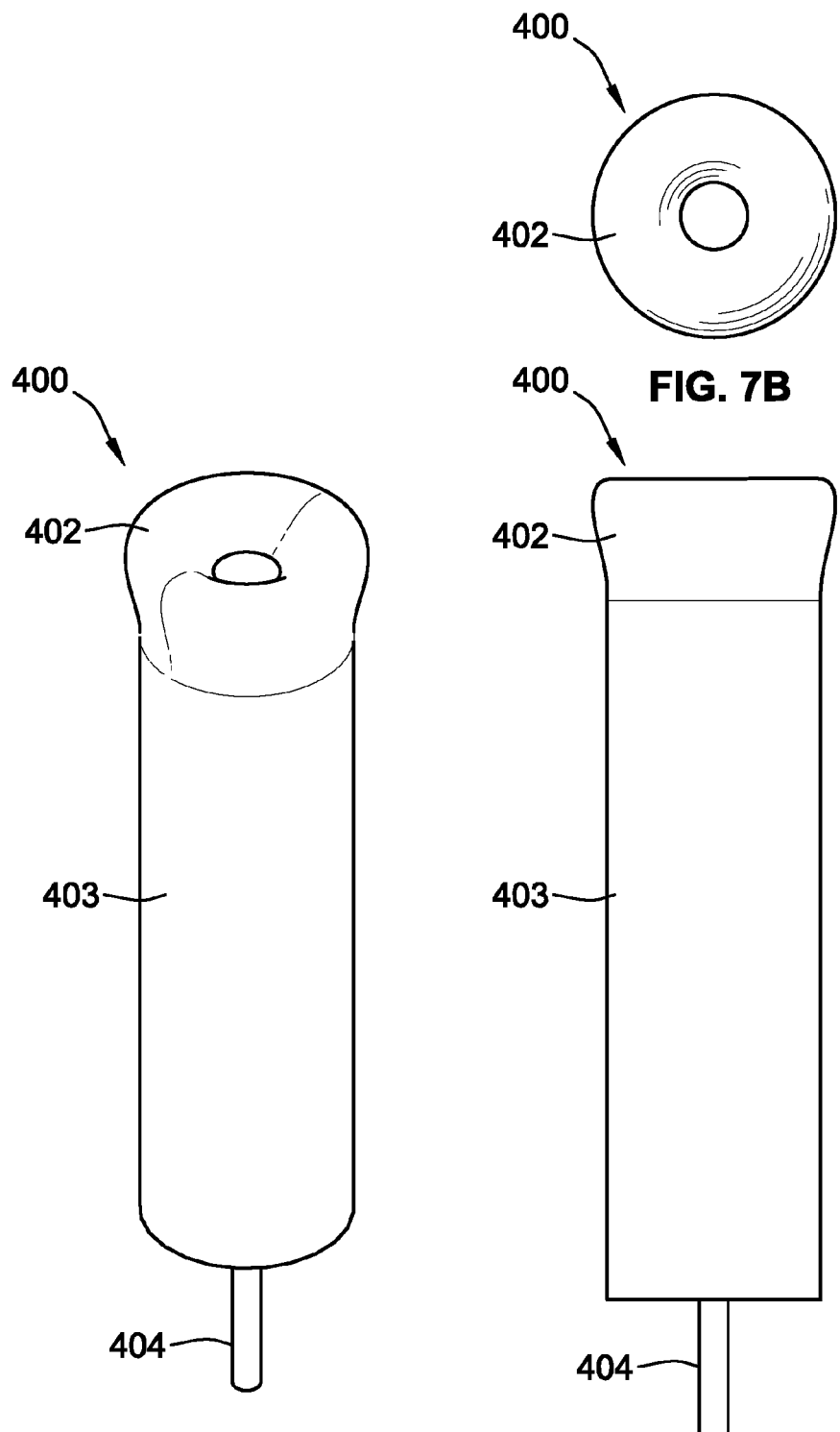

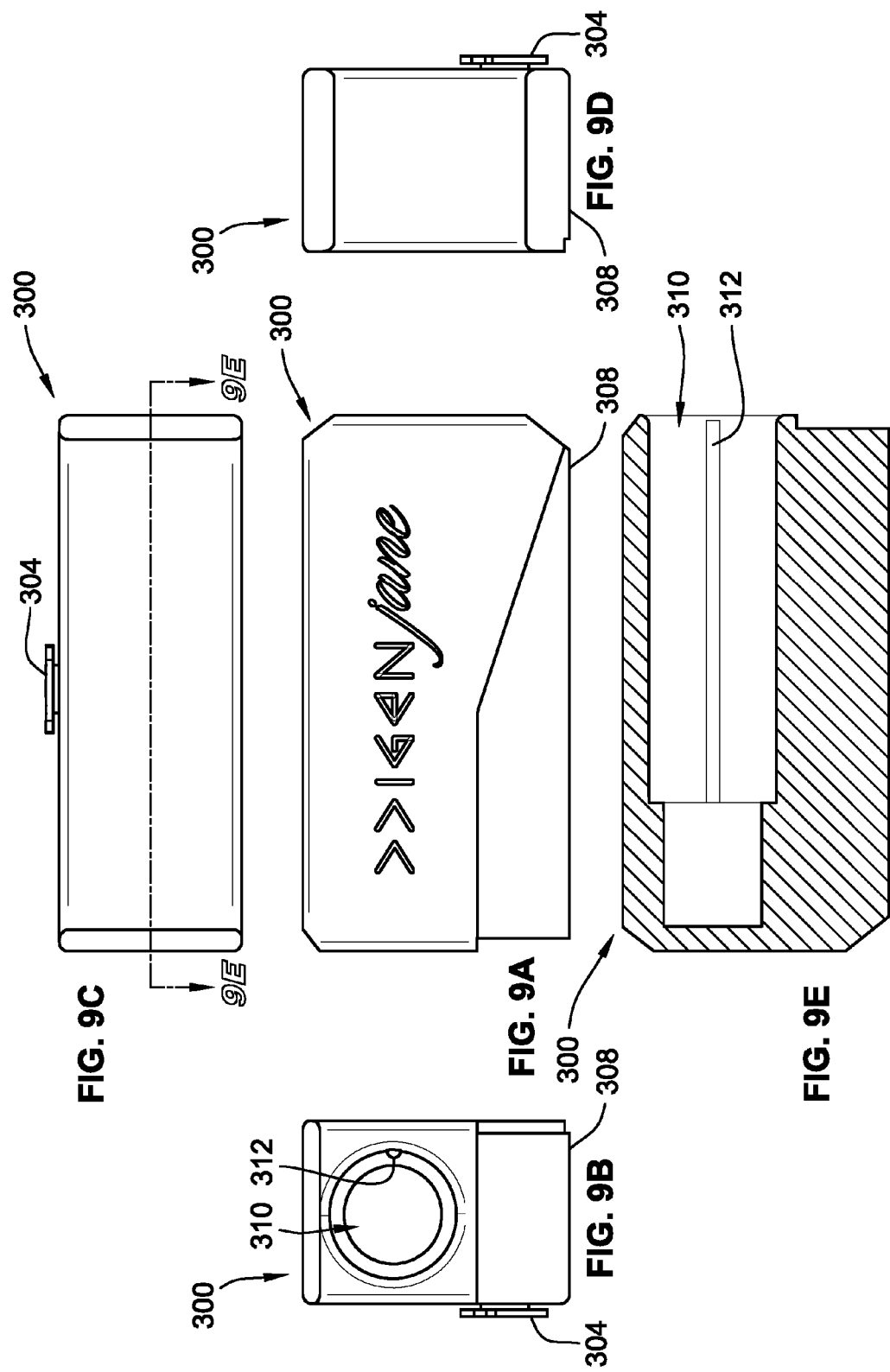

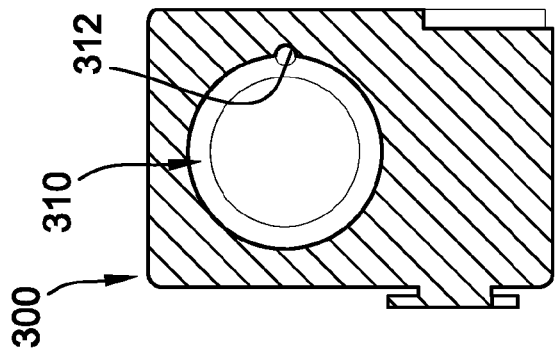
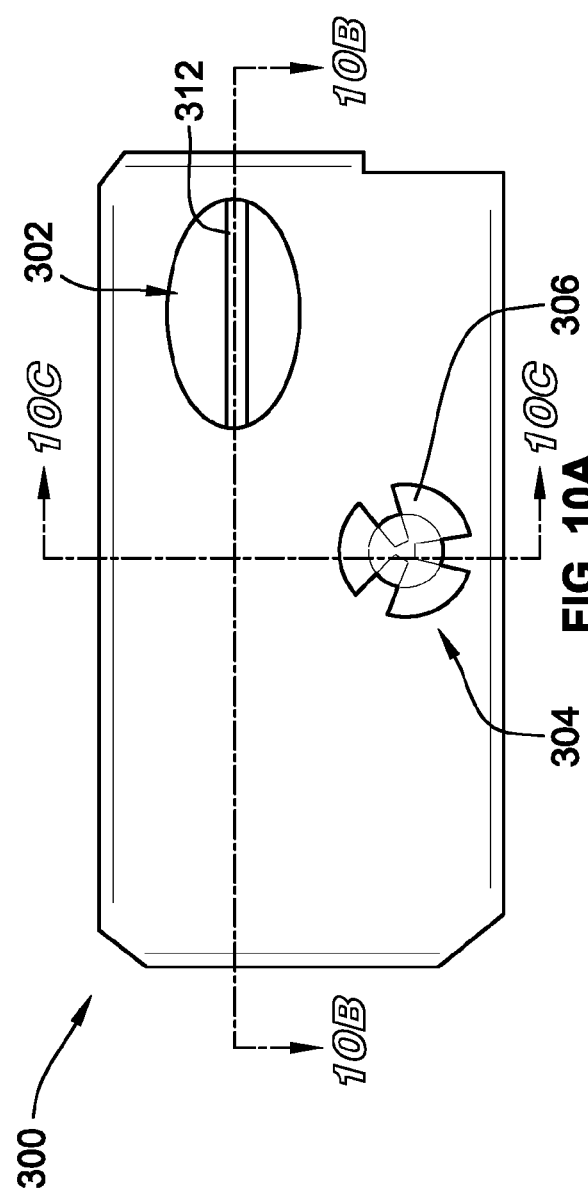
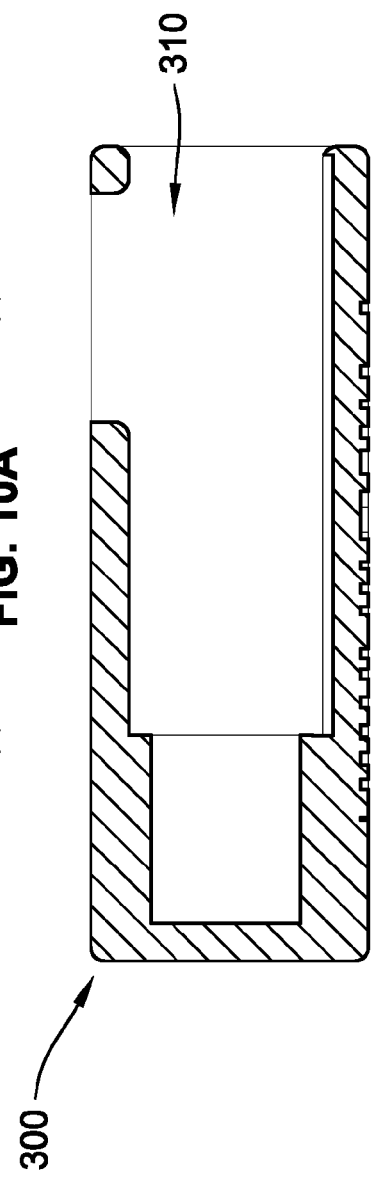

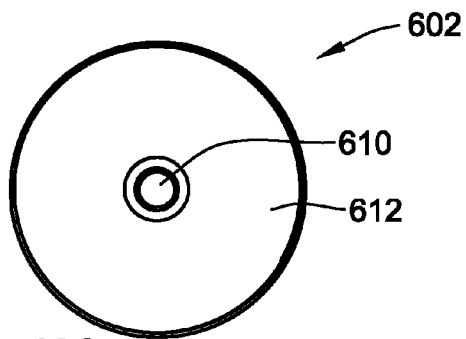
FIG. 12C
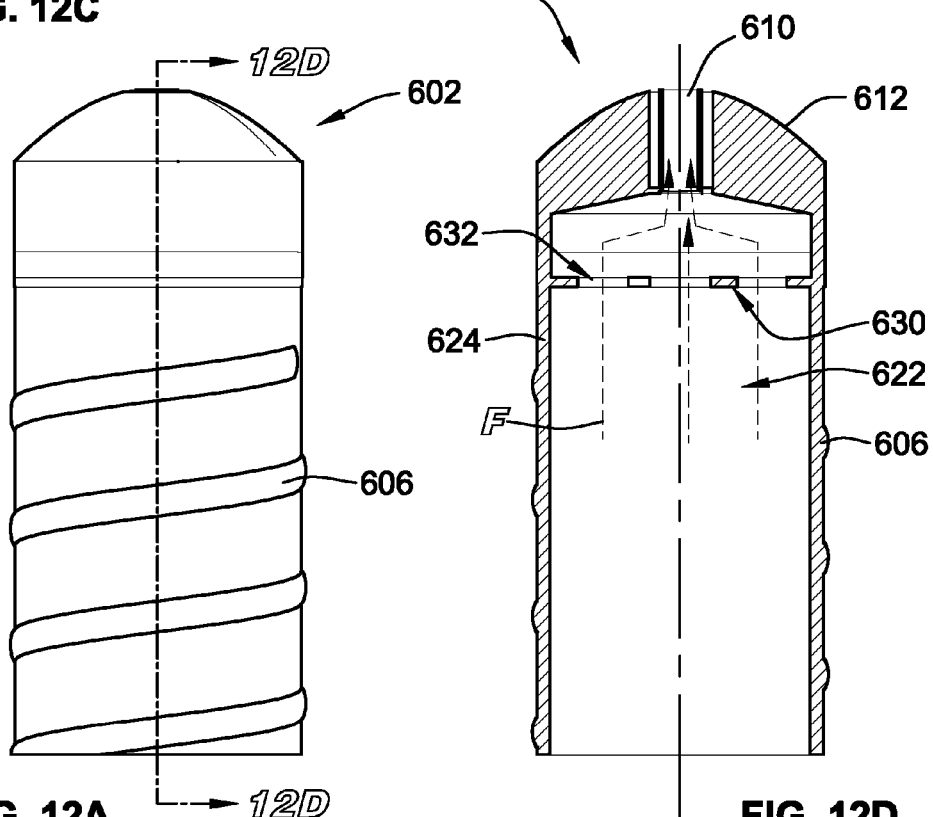
FIG. 12A
FIG. 12D
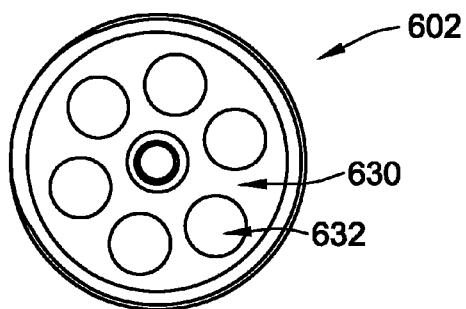
FIG. 12B

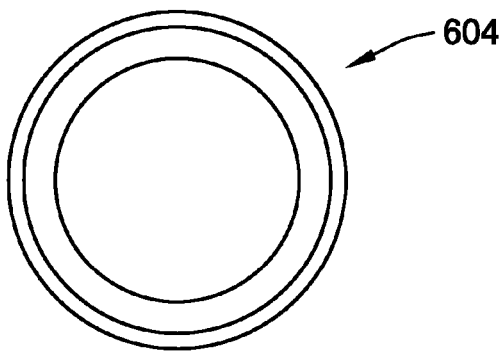
FIG. 13C
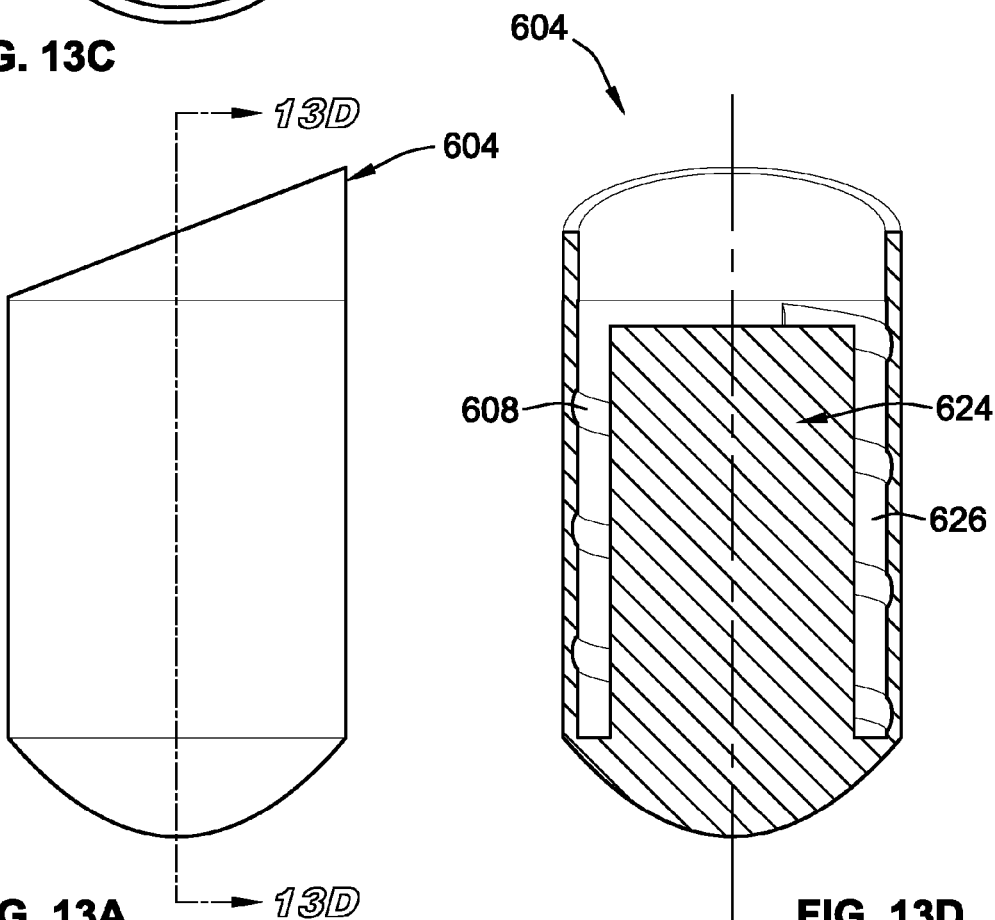
FIG. 13A
FIG. 13D
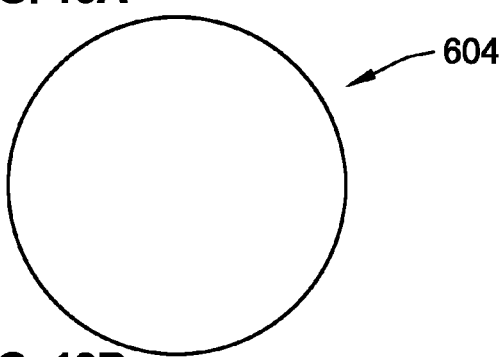
FIG. 13B

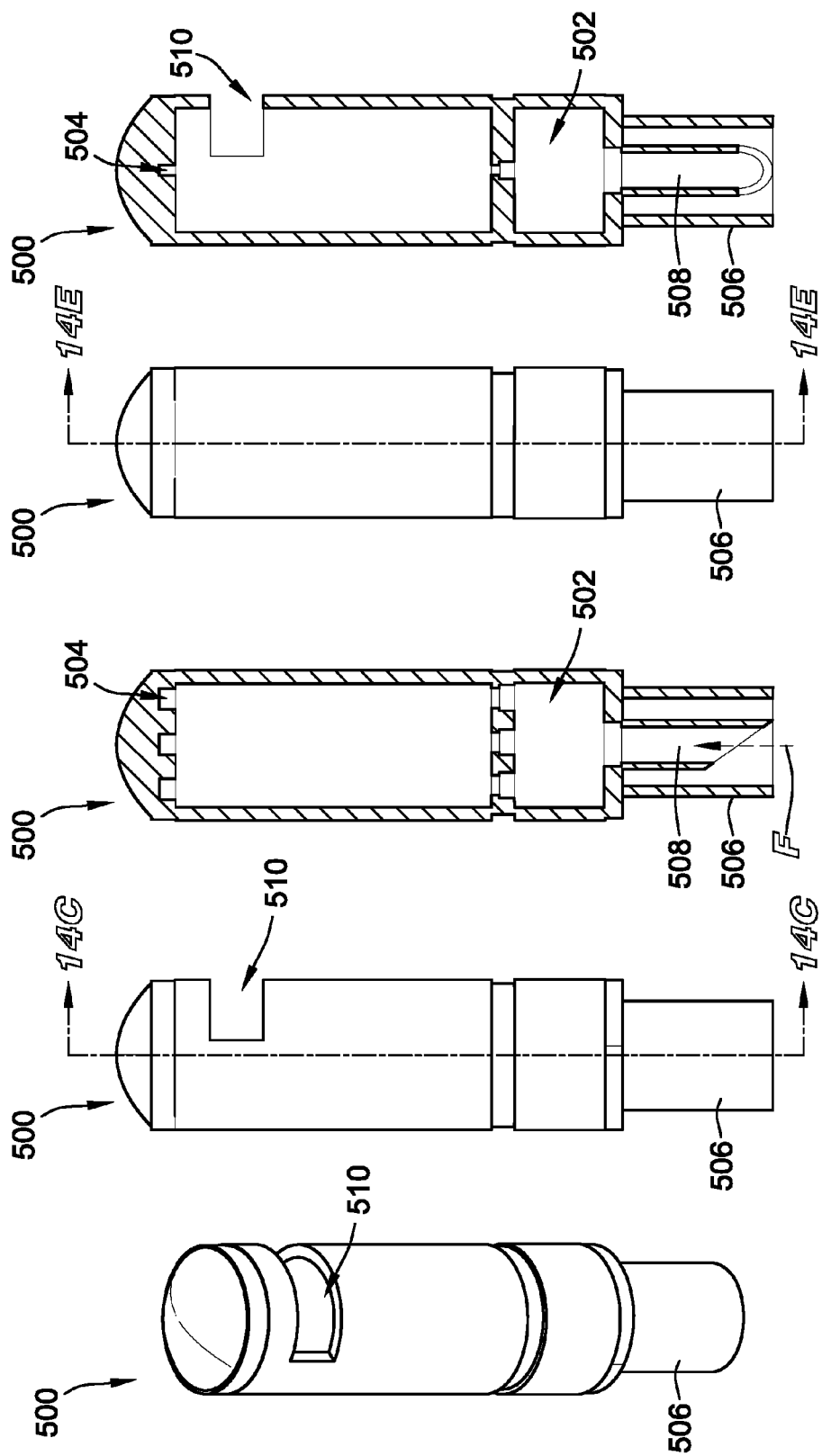

SYSTEM AND METHOD FOR MONITORING HEALTH BASED ON COLLECTED BODILY FLUID

CROSS-REFERENCE TO RELATED APPLICATIONS

This application is a continuation of International Patent Application No. PCT/US2015/044312, filed Aug. 7, 2015, which claims the benefit of U.S. Provisional Patent Application No. 62/036,469, filed Aug. 12, 2014, and the benefit of U.S. Provisional Patent Application No. 62/132,394, filed Mar. 12, 2015, the content of each of which is incorporated herein by reference in its entirety.

FIELD OF THE INVENTION

The present invention relates generally to a medical system for detecting and monitoring health conditions, and, more particularly, to a medical kit for collecting and analyzing biological samples from cervicovaginal fluid.

BACKGROUND OF THE INVENTION

Although accurate statistics on sexual assault are hard to come by, it is estimated that one out of every six American adult women has been the victim of an attempted or completed sexual assault in her lifetime. Considering the social stigma, shame, and fear associated with rape, it is not surprising that rape is the most under reported crime. Accordingly, semen detection tests, confirmatory tests and forensic DNA testing are indispensable tools for solving a case of rape and assault in order to bring perpetrators to justice.

Along these lines, five of the top ten reportable diseases in the United States are sexually transmitted diseases ("STDs"). Centers for Disease Control and Prevention ("CDC") estimates of February 2013 show that there are about 20 million new sexually transmitted infections ("STIs") in the United States each year, costing the American healthcare system nearly $16 billion in direct medical costs alone. CDC's data suggests that there are more than 110 million total (both new and existing) STIs among women and men across the nation. Young people (ages 15-24) are particularly affected, accounting for half (50%) of all new STIs. Some of these STIs have the potential to cause serious health problems, especially if not diagnosed and treated early.

STIs remain a major public health challenge in the United States, more so among women, who often disproportionately bear the long-term consequences of STIs. Women are more at risk for STIs due to the large surface area and the thin lining of the vagina. Women are more likely to be asymptomatic for common STIs and also have a greater biological susceptibility to infections. Women are also more likely to confuse an STI with a tame yeast infection or to have internal symptoms that may go unnoticed. STIs such as gonorrhea and chlamydia can lead to pelvic inflammatory disease ("PID") when left untreated. Chlamydia in particular can also cause asymptomatic infection of the fallopian tubes, and consequently, infertility. Furthermore, pregnant women have an increased risk of passing STIs to their babies, either during pregnancy or during vaginal birth.

Besides STIs, there are myriad health conditions that are important, not only to women's health, but also to long-term fertility management. Reproductive cancers such as cervical, ovarian, uterine, and endometrial are of particular concern as they are often asymptomatic and present in late stages of disease.

Many nutritional deficiencies such as folate, iron, and other vitamins are essential for the healthy development of the fetus, and anemia caused by deficiencies in these minerals can cause birth defects, allergy sensitizations, and preterm birth.

Many hormones that work in concert to provide the optimal environment for pregnancy and fertility can often become dysregulated and may prevent a woman from getting or staying pregnant. Dysregulation can also cause diseases such as endometriosis and polycystic ovarian syndrome that may prevent a woman from becoming pregnant.

Even during pregnancy there are many health factors that a woman can monitor to help reduce the risk for preterm birth and infections such as yeast infections and Strep B. Fetal Fribronectin, if found in vaginal secretions during 19-32 weeks of pregnancy can be indicative of a preterm birth.

A cascade of changes occur during perimenopause as women transition into their non-reproductive years that can be measured and provide information to women on what is going on in their bodies at a chemical level that may help inform them of health and lifestyle choices as they age.

Current blood-based diagnostic methods have reduced patient compliance because they require either a trip to an external facility, where a trained professional can perform venipuncture in a sterile environment, or a finger prick to collect a small aliquot of blood. Analysis of a blood sample is usually done in a laboratory by a different trained professional. Venipuncture in a doctor's office involves a non-trivial time commitment, travel and labor costs, and often psychological and physical pain that may prevent individuals from undergoing regular monitoring of blood-based health markers. Even finger pricks done at home can be psychologically daunting and are difficult to enforce on a regular basis. In addition, finger pricks produce only a small amount of blood and subsequently limit the types of diagnostics that can be run at home. The friction that blood acquisition, alone, introduces into the health-care system down regulates the vigor with which consumers proactively monitor their health.

Although other diagnostic techniques, such as the Papanicolaou ("Pap") smear do not require a blood sample, they still require a trip to the doctor's office. Current vaginal swab technologies require a specific swab that is inserted into the vaginal cavity. The protocol of collecting specimens from the vaginal cavity using a traditional vaginal swab is very precise, and an inaccurate procedure can lead to loss of sample and unreliable identification of desired biomarkers. Because of this, a trained medical professional typically administers vaginal swab collections. Moreover, the United States Preventive Task Force ("USPTF") currently recommends Pap smears only every three years. Even an annual checkup by an obstetrics and gynecology professional ("OB-GYN") does not guarantee a gonorrhea/chlamydia screen, nor would it be ideal to detect a pathogen that can lead to inflammation of the genital tract within weeks. This screening frequency impairs the identification and diagnosis of asymptomatic infections in particular.

As such, none of the currently available technologies allows for collection and analysis of biological materials for STIs in one device, without the need for further expensive laboratory equipment and professionals. One example of a currently available technology includes a method for screening for human papillomaviruses ("HPV"), and, in particular, screening for human genital papillomaviruses that are associated with neoplasia such as cervical cancer, which is described in International Patent Application Publication No. WO 2008/089519 to Tynan et al. ("Tynan"). Tynan's methods focus in particular on distinguishing between different HPV types in a biological sample. However, Tynan does not provide a device and method for self-analysis of one's blood samples. Samples must still be sent to a laboratory for diagnosis.

A portable device for the collection, storage, transport, and separation of biological materials is described in U.S. Patent Application Publication No. 2013/0337439 to Nobre et al. ("Nobre"). The materials can later be used to detect the presence of pathogens in a laboratory. However, the techniques offered require the use of acquired skills as well as expensive and specialized equipment.

In another publication by Tabrizi et al., the results of conventional methods for the detection of STIs are compared with results of tampon-collected specimens analyzed by polymerase chain reaction ("PCR") (*J. Infect. Dis.* 176: 289-292, 1997). However, as with the portable device taught by Nobre, all post-collection analysis work was done in a laboratory setting using specialized equipment.

The need to develop acceptable, accurate, and available point-of-care ("POC") tests for diagnosing sexually transmitted diseases (STDs) for all at-risk populations is significant. Stigma, privacy, and confidentiality issues make STDs/STIs optimal areas for POC tests at healthcare facilities and for over-the-counter assays performed at home.

Accordingly, there is a need for a medical system and method that solves these and other problems.

SUMMARY OF THE INVENTION

According to one aspect of the present invention, a medical kit for analysis of vaginal biological samples includes a sample collector, an extractor, and an assay cartridge. The sample collector is insertable in a vaginal canal for collecting biological samples and is compressible. The sample collector also includes a cup-shaped head configured to cradle a cervical os. The extractor includes a sample receptacle configured to receive the sample collector via an open end, and a compression mechanism with a compression element and a release element. The compression element is movable inwards into the open end of the sample receptacle to apply a compression force in response to activation of the release element. The extractor further includes a reservoir in fluid communication with the sample receptacle, the reservoir receiving the biological samples from the sample collector in response to the compression force being applied within the sample receptacle, through a filter that allows for purification of serum and other biological components from cellular debris. The assay cartridge has a docking mechanism configured to fluidly communicate with the reservoir of the extractor.

According to another aspect of the invention, a method for home-care monitoring of a health condition includes inserting a sample collector in a vaginal canal and collecting biological samples. The sample collector is removed from the vaginal canal and is placed inside a sample receptacle of an extractor. The sample collector is compressed within the sample receptacle by applying a force via a compression mechanism. In one embodiment, a diluent housed behind a punctureable membrane is released during the compression to wash the sample from the sample collector and release analytes of interest into the first chamber of the extractor. The biological samples are received from the sample collector into a reservoir of the extractor. An assay cartridge is docked in fluid communication with the reservoir, thereby allowing at least some of the biological samples to make contact with diluents or reagents of the assay cartridge. A health condition is determined based on a reaction between the biological samples and the diluents or reagents.

According to yet another aspect of the invention, a medical kit for analysis of biological samples includes a sample collector, an extractor, an assay cartridge, and a cartridge reader. The sample collector is insertable in a body cavity for collecting biological samples, is compressible, and includes an absorbent-diffuse material for absorbing and releasing fluids. The extractor acquires the biological samples from the sample collector, and includes a receptacle in which the sample collector is received. The extractor includes a compression mechanism for applying a force within the receptacle to release the biological samples from an inserted sample collector. The assay cartridge has an extractor interface and a reader interface, the extractor interface being configured to be coupled in fluid communication with the extractor. The biological samples are transferred from the extractor to the assay cartridge via the extractor interface. The cartridge reader has a cartridge interface configured for interfacing with the reader interface, the cartridge reader receiving assay data from the assay cartridge and communicating at least some of the assay data to a mobile device via a mobile interface.

According to yet another aspect of the invention, a disclosed sample-collection method and device utilizes proprietary and/or widely available commercial tampons without the need for a special swab that is not widely available to the consumer. The sample-collection device also promotes correct insertion into the vaginal cavity and promotes more accurate and efficient collection of specimen due to its large surface area and precise contour. The sample-collection device further collects a larger volume of specimen than traditional vaginal swabs allowing for a more accurate analysis of the specimen and higher probability of capturing biomarkers or analytes of interest.

According to yet another aspect of the invention, a sample collection device for analysis of the cellular components of the vaginal canal, in which a removable filter cassette housed within the extractor filters out cellular components of cervicovaginal fluid including blood, cervical, endometrial, fallopian, ovarian, and trophoblast cells for analysis through microscopy or other cellular imagine technologies for assessment of the health of reproductive cells within the biological matrix collected through the collection device.

According to yet another aspect of the invention, a sample-collection device is suitable for regular and painless collection of cervicovaginal fluid and rich biological matrix without the need for skin puncture or a skilled technician. The sample-collection device is optionally included in a medical kit that provides a simple diagnostic assay that can be run in the privacy of one's home.

According to yet a further aspect of the invention, a device and method is directed to self-analysis of one's cervicovaginal fluid samples for pathogens, hormones, protein analytes (indicative of health status), mineral levels, genetic material (indicative of disease, disorders, or predispositions thereof), or the presence of semen.

According to yet a further aspect of the invention, a sample-collection device for regular, easy collection of specimen from the vaginal cavity. The sample collection kit may include preservation buffers to maintain sample quality for a mail-in service. The sample is optionally processed and analyzed in a centralized lab and results delivered to the customer at a later date.

Additional aspects of the invention will be apparent to those of ordinary skill in the art in view of the detailed description of various embodiments, which is made with reference to the drawings, a brief description of which is provided below.

BRIEF DESCRIPTION OF THE DRAWINGS

FIG. 3 is an exploded perspective view of an extraction device, in accordance with one exemplary embodiment.

FIG. 4A is a side view of an extraction device, in accordance with another exemplary embodiment.

FIG. 4B illustrates a spring-loaded compressor of the extraction device shown in FIG. 3A.

FIG. 4C illustrates a reservoir of the extraction device shown in FIG. 3A.

FIG. 6A is a front view of the snap-on adapter shown in FIG. 5A.

FIG. 6B is a left view of the snap-on adapter shown in FIG. 5A.

FIG. 6C is a bottom view of the snap-on adapter shown in FIG. 5A.

FIG. 6D is a right view of the snap-on adapter shown in FIG. 5A.

FIG. 6E is a top view of the snap-on adapter shown in FIG. 5A.

FIG. 7A is a perspective view of a sample collector, in accordance with one exemplary embodiment.

FIG. 7B is a top view of the sample collector shown in FIG. 7A.

FIG. 7C is a side view of the sample collector shown in FIG. 7A.

FIG. 9A is a front view of the assay reader shown in FIG. 8A.

FIG. 9B is a left view of the assay reader shown in FIG. 8A.

FIG. 9C is a top view of the assay reader shown in FIG. 8A.

FIG. 9D is a right view of the assay reader shown in FIG. 8A.

FIG. 9E is a cross-sectional view along lines "9E-9E" of FIG. 9C.

FIG. 10A is a back view of the assay reader shown in FIG. 8A.

FIG. 10B is a cross-sectional view along lines "10B-10B" of FIG. 10A.

FIG. 10C is a cross-sectional view along lines "10C-10C" of FIG. 10A.

FIG. 12A is a side view of the extractor top shown in FIG. 11.

FIG. 12B is a bottom view of the extractor top shown in FIG. 11.

FIG. 12C is a top view of the extractor top shown in FIG. 11.

FIG. 12D is a cross-sectional view along lines "12D-12D" of FIG. 12A.

FIG. 13A is a side view of the extractor bottom shown in FIG. 11.

FIG. 13B is a bottom view of the extractor bottom shown in FIG. 11.

FIG. 13C is a top view of the extractor bottom shown in FIG. 11.

FIG. 13D is a cross-sectional view along lines "13D-13D" of FIG. 13A.

FIG. 14A is a perspective view of an assay cartridge, in accordance with one exemplary embodiment.

FIG. 14B is a side view of the assay cartridge shown in FIG. 14A.

FIG. 14C is a cross-sectional view along lines "14C-14C" of FIG. 14B.

FIG. 14D is a back view of the assay cartridge shown in FIG. 14A.

FIG. 14E is a cross-sectional view along lines "14E-14D" of FIG. 14D.

Figure 1:
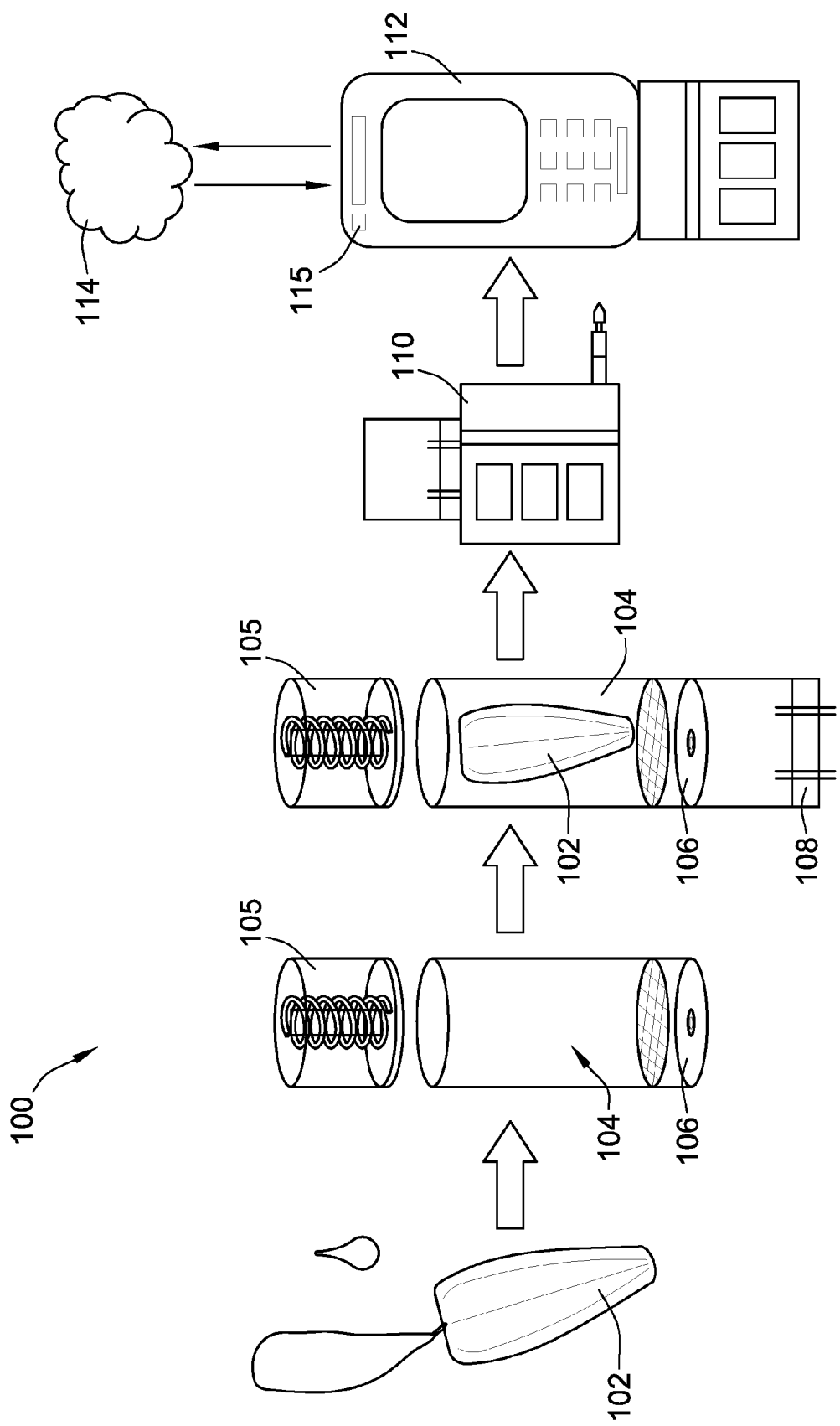
FIG. 1 is a schematic view illustrating a method and system for collecting and analyzing a biological sample.

While the invention is susceptible to various modifications and alternative forms, specific embodiments have been shown by way of example in the drawings and will be described in detail herein. It should be understood, however, that the invention is not intended to be limited to the particular forms disclosed. Rather, the invention is to cover all modifications, equivalents, and alternatives falling within the spirit and scope of the invention as defined by the appended claims.

DETAILED DESCRIPTION

While this invention is susceptible of embodiment in many different forms, there is shown in the drawings and will herein be described in detail preferred embodiments of the invention with the understanding that the present disclosure is to be considered as an exemplification of the principles of the invention and is not intended to limit the broad aspect of the invention to the embodiments illustrated.

Definitions

Unless defined otherwise, all technical and scientific terms used in this disclosure have the same meanings as commonly understood by one of ordinary skill in the art to which this disclosure belongs.

As used herein the term "comprising" or "comprises" is used in reference to compositions, methods, and respective component(s) thereof, that are essential to the invention, yet open to the inclusion of unspecified elements, whether essential or not.

The singular terms "a," "an," and "the" include plural referents unless context clearly indicates otherwise. Similarly, the word "or" is intended to include "and" unless the context clearly indicates otherwise.

Other than in the operating examples, or where otherwise indicated, all numbers expressing quantities of ingredients or reaction conditions used herein should be understood as modified in all instances by the term "about." The term "about" when used in connection with percentages may mean±5% of the value being referred to. For example, about 100 means from 95 to 105.

Although methods and materials similar or equivalent to those described herein can be used in the practice or testing of this disclosure, suitable methods and materials are described below. The term "comprises" means "includes." The abbreviation, "e.g." is derived from the Latin exempli gratia, and is used herein to indicate anon-limiting example. Thus, the abbreviation "e.g." is synonymous with the term "for example."

As used herein the term "consisting essentially of" refers to those elements required for a given embodiment. The term permits the presence of elements that do not materially affect the basic and novel or functional characteristic(s) of that embodiment of the invention.

The term "assay" as used herein refers to the analysis of a sample to determine the presence, absence, quantity or edited nature of one or more components.

The term "assay cartridge" as used herein refers to the part of the device that contains the diluents, materials, and reagents necessary for testing for certain markers. This cartridge inserts into the pressure valve of the reservoir end of the extractor, thus enabling the transfer of cervicovaginal fluid from the reservoir to the assay cartridge, where the cervicovaginal fluid comes into contact with the diluents and reagents.

The term "binary readout" as used herein refers to the results given by the cartridge reader that are expressed as either "positive" or "negative."

The term "quantitative readout" as used herein refers to a reported measurement of a specific quantity of a substance and reflects an absolute amount or concentration.

The term "cartridge reader" as used herein refers to the part of the device that connects with the assay cartridge and gives a binary or quantitative readout of the test result.

The term "cradle" as used herein refers to how the sample collector fits against the os of the cervix. The fit can be partial or full, as long as the device absorbs fluid readily.

The term "dense" as used herein refers to the state of being closely compacted.

The terms "extractor" or "extraction device" as used herein refers to the part of the device that includes the sample collector receptacle, optionally a puncturable membrane containing diluent or buffer, and the reservoir. A filter separates the receptacle and the reservoir, and a pressure valve at the bottom of the reservoir enables attachment of the assay cartridge and subsequent transfer of the cervicovaginal fluid into the cartridge. The extractor, optionally, also has a cap that houses a spring-loaded compressor and a button, which, if pushed, compresses the sample collector, thereby allowing the cervicovaginal fluid from the sample collector to pass through the filter into the reservoir.

The term "filter" as used herein refers to the porous material between the sample collector receptacle and the reservoir, which serves to remove endometrial tissue, red blood cells, peripheral blood mononuclear cells and other cellular debris from the extracted sample to ultimately yield the filtered cervicovaginal fluid, as well as purified cellular material on the filter, which can be removed for downstream analysis.

The term "mobile interface" as used herein refers to an interactive mobile application which ties the data acquisition facilitated by the device to comprehensive behavioral management.

The term "sample collector" as used herein refers to a device that is inserted into the vagina to absorb cervicovaginal fluids and can both absorb quickly as well as release fluid with ease. Alternatively, a sample collector may be configured to collect cervicovaginal fluids outside the body.

The term "optimal" as used herein refers to the most favorable outcome.

The term "os of the cervix" or "cervical os" as used herein refers to the opening of the uterine cervix which is covered by squamous epithelium.

The term "permeated thread matrix" as used herein refers to a thread matrix that is spread throughout the inner shell of the sample collector.

The term "plant fiber" as used herein refers to any fibers, threads, ribbons, or beads that are absorbent in nature.

The term "pressure valve" as used herein refers to the cylindrical pipe connected to the bottom of the reservoir. In one embodiment, this is a normally closed, low pressure, one-way check valve with a luer slip that facilitates the unidirectional movement of the filtered cervicovaginal fluid from the reservoir to the assay cartridge, and prevents back flow when the luer slip is engaged. Insertion of the assay cartridge and application of low pressure opens the valve.

The term "reinforced" as used herein refers to the state of being strengthened and supported so as to reduce leakage.

The term "reservoir" as used herein refers to the part of the extractor which receives the filtered blood or cervicovaginal fluid after it passes through the filter from the sample collector receptacle.

The term "spring-loaded compressor" as used herein refers to the elastic device inside the extractor cap, which compresses the tampon, thereby allowing the cervicovaginal fluid from the tampon to pass through the filter into the reservoir.

The term "sample receptacle" as used herein refers to the part of the extractor which houses the used tampon.

The term "time-independent signal amplification immunoassay" as used herein refers to an immunoassay for the detection of analytes which can be flexibly conducted without rigid adherence to time limits or storage conditions.

The term "tooth-like shape" as used herein refers to two projections at the tip of the feminine hygiene device that configure it to fit the cervical os.

The term "cervicovaginal fluid" as used herein refers to any biological fluids and/or matrix contained within or expelled from the vagina, such as blood, semen, vaginal mucosa, interstitial fluid, cervical secretions, or shed reproductive, endometrial and fetal tissues, or any combination thereof.

The term "web-based interface" as used herein refers to a website that facilitates bi-directional communication with a target audience.

Components

One purpose of the collection device is to use cervicovaginal fluid to regularly provide women with informative data about their health so that they can better and more accurately assess the complex nature of their personal fertility and overall well-being.

Referring to FIG. 1, a representative and exemplary system 100 includes at least a few of the following five components: a specialized sample collector 102 (illustrated by way of example in the form of a tampon) to optimize collection of cervicovaginal fluid for testing; a biological matrix extractor 104 with a compression top 105 to pull fluid, vaginal mucosa, or semen into an assay delivery reservoir 106, through a filter 150; an assay cartridge 108 to evaluate the biological content of the biological matrix; a cartridge reader 110 which automates assay development, result capture, and result interpretation; and a mobile app interface 112 (illustrated by way of example on a mobile phone with a camera 115) that interprets and tracks a user's results and curates validated recommendations for health and behavior. The cartridge reader may electronically interface with the mobile phone by plugging into a headphone jack on the mobile phone. Optionally, a web-based interface 114 can provide access to easy interventions like food shopping, vitamin stores, and health facilities for therapeutics, and provides a positive behavioral feedback loop to increase prevention adherence.

1. Sample Collector

Figure 2:
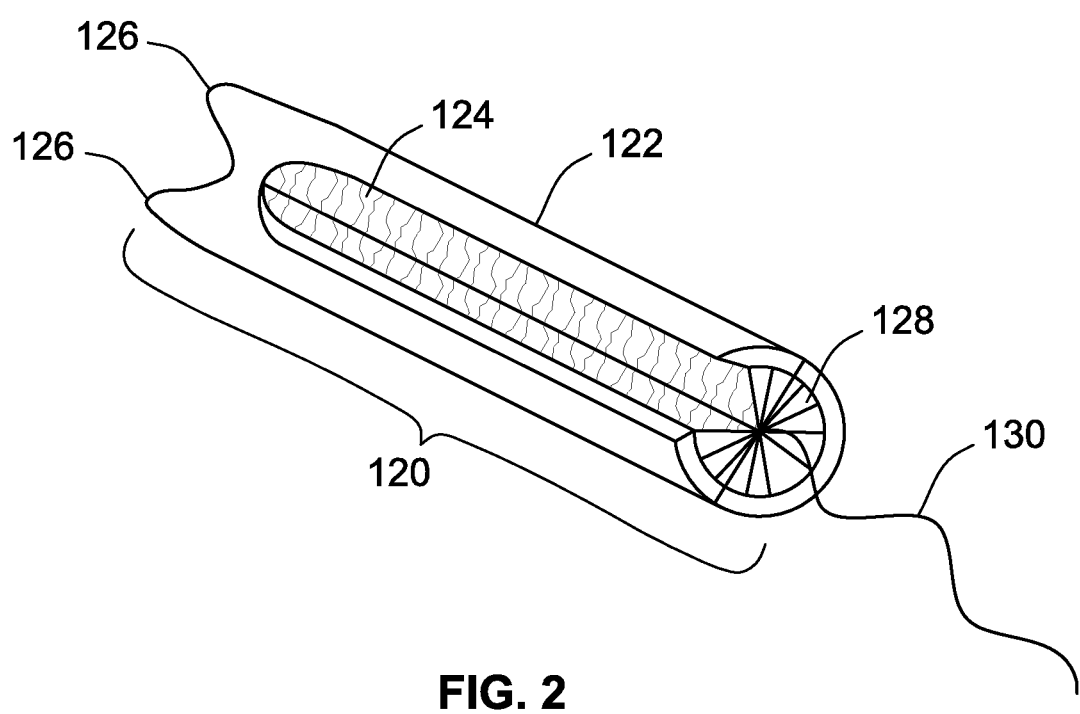
FIG. 2 is a partial cross-sectional perspective view of a feminine hygiene device, in accordance with one exemplary embodiment.
Figure 5B:
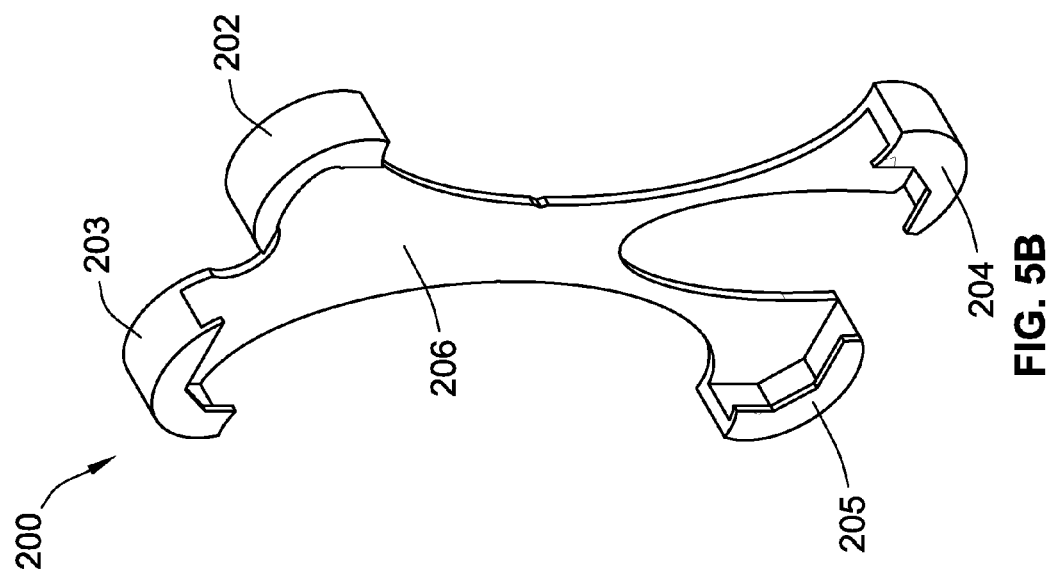
FIG. 5B is a back perspective view of the snap-on adapter shown in FIG. 5A.
Figure 5A:
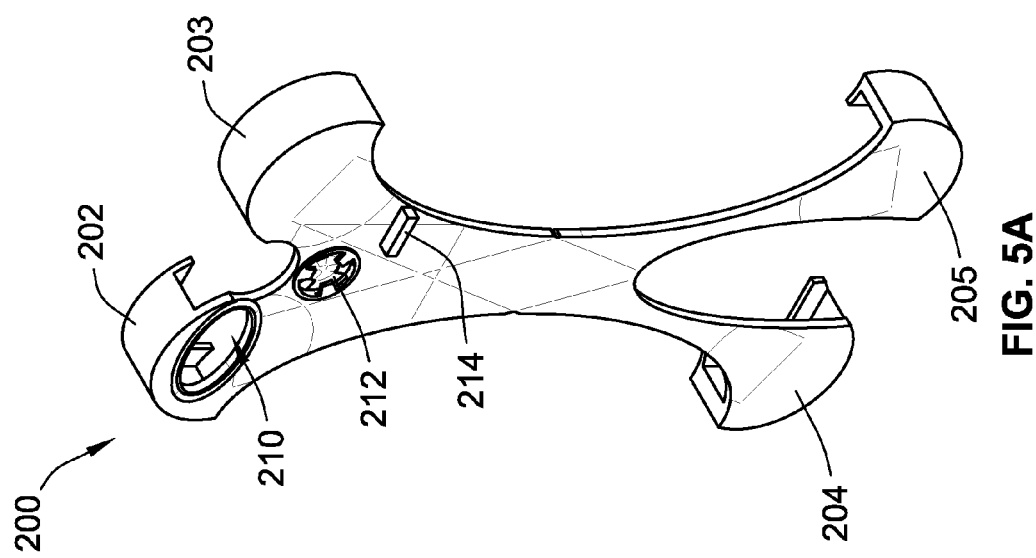
FIG. 5A is a front perspective view of a snap-on adapter for attachment of an assay cartridge to a mobile telephone, in accordance with one exemplary embodiment.

Referring to FIG. 2, a sample collector 120 is configured to be inserted into a human body cavity (e.g., the vagina or vaginal canal), in accordance with one exemplary embodiment. Such use of the sample collector 120 has facilitated rapid device design and implementation. The sample collector 120 absorbs quickly and releases fluid with ease, as the volume of cervicovaginal fluid can vary for every woman. This sample collector includes a dense outer shell 122 of absorbent plant fiber. The plant fiber is of similar construction and make as that in a commercially available tampon. In other embodiments, the plant fiber is flax, hemp or bamboo.

An inner shell 124 of the sample collector is not dense, but it is diffusely permeated with a thread matrix. The threads provide enough structure to help the sample collector maintain its shape and function. However, the threads are also distributed in the inner chamber in such a manner as to facilitate collapse upon pressure via the extractor. This sample collector soaks up fluid readily, but also compresses easily to release fluid. In some embodiments, a tip 126 of the sample collector has a tooth-like shape that is bifurcated to specifically cradle the os of the cervix. This design maximizes correct placement of the sample collector around the os for optimal specimen collection. A base 128 of the sample collector is composed of multiple layers of absorbent plant fiber material that form a reinforced seal to prevent leakage.

In some embodiments, the sample collector has a means for pulling 130 that attached to the base 128. In some embodiments, the means for pulling 130 is a loop or a knot. In some embodiments, the means for pulling 130 is a string. In a preferred embodiment, the sample collector is included in a monthly kit.

Referring to FIGS. 7A-7C, a sample collector 400 is configured to be inserted into a human body cavity (e.g., the vagina or vaginal canal), in accordance with one exemplary embodiment. For example, the sample collector 400 is a cylinder having a head 402 configured to cradle the os of the cervix. Opposite to the head 402, and separated by a main body 403, the sample collector 400 has a removal element 404 via which it is removed from the body cavity, e.g., by pulling on the removal element 404. By way of example, the removal element 404 is a string.

The sample collector 400 includes a material configured to release collected biological samples, such as cervicovaginal fluids, and may include a hydrogel material and/or a dissolvable material. According to one embodiment, the sample collector 400 is a cotton or other organic fiber-based apparatus that is inserted into the vaginal canal for the purpose of collecting biological samples. The sample collector 400 collects menstrual fluid, reproductive tissue, mucosa, and foreign bodies. The sample collector 400 is absorbent but diffuse, to readily absorb and release fluids. For example, the sample collector 400 is disposable, flushable, biodegradable, organic, or natural. The sample collector 400 is configured to be removed via a string, a loop, or other handle, and is configured for insertion via an outer shell applicator.

Optionally, instead of being configured to be inserted into a body cavity, the sample collector is configured to collect or absorb biological samples such as cervicovaginal fluids external to the body. Non-limiting examples include a cup or receptacle (e.g., a diva cup or a funnel with a reservoir) and/or an external absorber (e.g., an absorbent pad or a reusable cloth). In some embodiments, the external sample collector is composed from the materials described herein for internal sample collectors, and soaks up fluid readily, but also compresses easily to release fluid.

2. Extractor

In an embodiment shown in FIGS. 3 and 4A-4C, an extraction device is included in the kit and includes a cylindrical housing or receptacle 140 in which a woman places her used sample collector 120 via an open end 142 immediately upon removal from the vaginal canal. The extraction device is then sealed with a cap 144, which contains a spring-loaded compressor 146. After the extraction device is sealed, a button 148 located on the cap 144 is pressed, which releases the spring 146 and compresses the sample collector 120.

In some embodiments, a twist mechanism is employed to compress the sample collector 120. As the sample collector 120 is compressed, cervicovaginal fluid, blood, vaginal mucosa, or semen are squeezed out and passed through a filter 150 to remove cellular debris or mucosa that may clog the pressure valve leading to the assay cartridge. In some embodiments, the pore size of the filter 150 is 10 microns, 25 microns, or 40 microns. In other embodiments, the diameter of the filter 150 is between 28 mm and 30 mm. The sample collector and filter retain most of the endometrial tissue and cervicovaginal fluids. However, some of the vaginal mucosa and possibly un-clotted red blood cells are sheared through the extraction process. This shearing of vaginal mucosa allows for intracellular organisms to be passed through the filter into a sample collection reservoir 152 along with the extracted cervicovaginal fluid.

In some embodiments, a series of filters with sequentially decreasing pore size are present in the extractor. The filters collect analytes of various sizes, starting with larger analytes such as whole cells, and decreasing in size to cell fragments, organelles and macromolecules (e.g., proteins, nucleic acids, carbohydrates, lipids, etc.). Optionally, the filters are individually removable so the analytes of various sizes may be separately assayed, either using the assay cartridge or packaged and sent to an outside lab. In some embodiments, a filter is sized to separate out sperm cells so that the sperm cells may be sent to an outside lab for DNA analysis.

In some embodiments, the serum or sample collection reservoir may be divided into two or more detachable compartments, such that each compartment can store an aliquot of a sample for storage and/or for different downstream analyses without contamination. For example, one compartment may be detached and sent to an outside lab for more detailed analysis, if needed.

Within the walls of the sample collection reservoir is a pressure valve 154 that inserts into the assay cartridge, thereby allowing for one-way passage of the extracted fluids into the assay cartridge. In some embodiments, the valve opens under a pressure of between 1.5 pounds per square inch ("PSI") and 5 PSI. For example, the valve opens under a pressure of 1.5 PSI, 3 PSI or 5 PSI. In some embodiments, the valve has a diameter of between 3 mm and 5 mm.

In some embodiments, a press-lever mechanism is employed to compress the sample collector 120. In some embodiments, a manual-push mechanism is employed to compress the sample collector 120. In some embodiments, an air-tight plunger mechanism is employed to compress the sample collector 120. In some embodiments, a pressure-based mechanism is employed to compress the sample collector 120. In some embodiments, a roller-based mechanism is employed to compress the sample collector 120. In some embodiments, a compressible chamber is employed to compress the sample collector 120.

Figure 11:
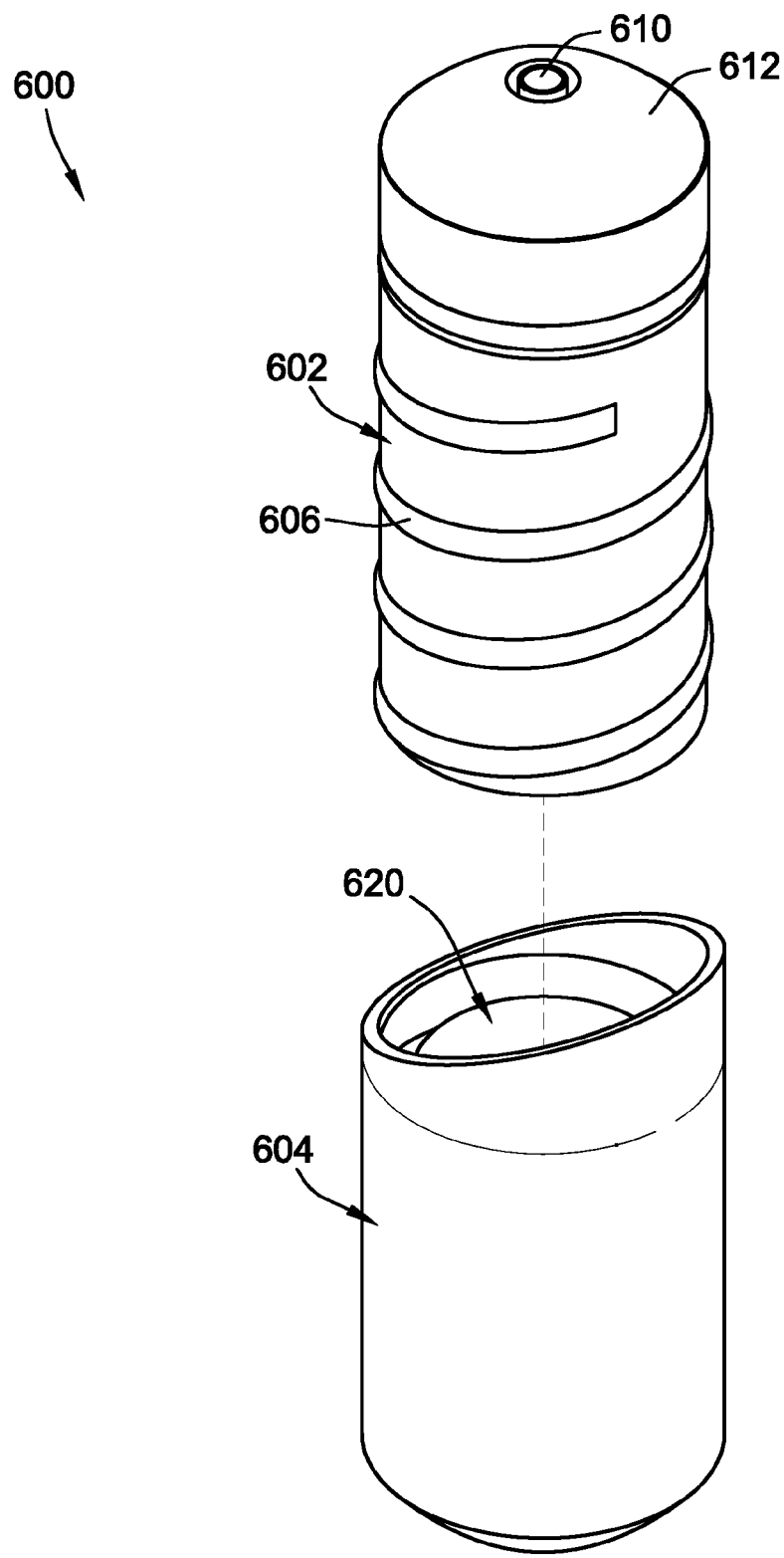
FIG. 11 is an exploded perspective view of an extractor system with an extractor top and an extractor bottom, in accordance with one exemplary embodiment.

In an embodiment shown in FIGS. 11-13, an extractor system 600 includes an extractor top 602 and an extractor bottom 604. The extractor top 602 includes an external thread 606 that is configured to threadedly engage an internal thread 608 of the extractor bottom 604 as the extractor top 602 is rotated inserted within the extractor bottom 604. The extractor top 602 further includes a fluid port 610 centrally located along a top surface 612 via which biological fluids or other samples from within the extractor system 600 are communicated to the assay cartridge 500 (shown in FIGS. 14A-14E). In some embodiments, the fluid port comprises a Luer lock valve, a one-way pressure valve, or a rubber resealable puncture slit.

The extractor system 600 has a sample receptacle 620 configured to receive a sample collector, such as the sample collector 400 illustrated in FIGS. 7A-7C. The sample receptacle 620 includes a top receptacle 622 and a bottom receptacle 624. The top receptacle 622 is within the extractor top 602 and is generally defined by top wall 624 of the extractor top 602. The bottom receptacle 624 is within the extractor bottom 604 and is generally defined by a bottom wall 626.

When a sample collector is placed within the sample receptacle 620 and the extractor top 602 is threaded within the extractor bottom 604, the resulting compressive force squeezes the sample collector causing it to release collected biological fluids F. In turn, at least some of the biological fluids F are directed to flow towards the fluid port 610, passing through an optional filter 630 located in the extractor top 602. The filter 630 includes a plurality of pass-through holes 632 through which the fluid F exits towards the fluid port 610.

Although the above-described extractor system 600 is generally a screw-based compressor, in alternative embodiments the extractor system is optionally a pressure-based compressor, a spring-loaded compressor, a roller-based compressor, a press-lever compressor, a manual push compressor, or an air-tight plunger compressor. These various, different mechanical configurations are capable of extracting fluid from a sample collector. Optionally, one or more configurations include a compressible chamber.

In other alternative embodiments, the filtration of the sample includes a filter of a specific pore size, a combination of filters, filter components that specifically bind hemoglobin, paper-based filters, silica filters, and/or microfluidic filters. In yet other alternative embodiments, the extractor system 600 includes one or more buffers to dilute the sample to minimize background noise in the downstream assay, buffers with exogenous control compounds, buffers with spike-ins to normalize downstream data outputs, buffers to aid in elution of biological fluid, buffers to extract particular biological components (e.g., DNA, RNA, proteins, etc.), buffers to precipitate or otherwise remove hemoglobin or other biological components that could interfere with assay or results (e.g. $ZnSO_4$, etc.), buffers to bind and remove particular biological components, buffers to hydrolyze or dissolve the sample collector, buffers that are lyophilized, buffers that are housed in dissolvable membranes, and/or buffers that are housed in a puncturable or breakable membrane. In further alternative embodiments, the extractor system 600 includes components that are biodegradable and/or recyclable. In yet further alternative embodiments, the extractor system 600 has a sample outflow in which the outlet valve (e.g., the fluid port 610) has a rubber resealable puncture slit and/or a one-way pressure valve luer lock valve.

3. Assay Cartridge

In certain embodiments, the assay cartridge is a small, cuvette-shaped device that contains diluents, reagents, test strips, and other necessary chemistries for testing of the presence of certain fungi, bacteria, viruses, viroids, parasites, protozoa, biological markers present on these pathogens, markers present on molecules produced or induced by these pathogens, or antibodies produced in response to infection. In some embodiments, the assay detects STIs. In a preferred embodiment, the STIs are gonorrhea and chlamydia. In other embodiments, the assay detects markers indicative of cancer, e.g. breast cancer, cervical cancer, ovarian cancer, uterine cancer, endometrial cancer, fallopian tube cancer, etc. In yet other embodiments, the assay detects markers present in semen, e.g. prostate-specific antigen (PSA), prostatic acid phosphatase (PAP), etc. The reagents can also be used to measure hormone levels, detect pregnancy, or indicate other disease or disorders. In some embodiments, the assay detects markers indicative of fertility, e.g., luteinizing hormone (LH), follicle-stimulating hormone (FSH), anti-Mullerian hormone (AMH), thyroid-stimulating hormone (TSH), progesterone, etc. In some embodiments, the assay detects markers indicative of pre-pregnancy health and/or nutrition, e.g., TSH, bisphenol-A (BPA), iron, folate, vitamin D, etc. In some embodiments, the assay detects markers indicative of pre-term birth, e.g., pH, fetal fibronectin (fFN), cathepsin-E, etc. In some embodiments, the assay detects markers indicative of endometriosis and polycystic ovarian syndrome. In some embodiments, the assay detects markers indicative of yeast infections, bacterial vaginosis, and alcohol abuse.

In some embodiments, the assay cartridge is configured to run a plurality of assays from a single sample. Preferably, the assay cartridge may be configured to run 2, 3, 4, 5, 6, 7, 8, 9, 10 or more assays either in parallel or in series.

The assay cartridge forms the backbone of this at-home testing device, and allows for expansion of future biomarkers that are aimed at long-term fertility management and pre-pregnancy health. As mentioned above, the assay cartridge is completely self-contained. The pressure valve located at the bottom of the reservoir/extractor is pushed down once it is docked with the assay cartridge, allowing a small amount of cervicovaginal fluid to enter into the assay cartridge.

Once the cervicovaginal fluid has transferred to the assay cartridge, the cartridge is undocked from the reservoir/extractor. In some embodiments the extractor device is reused. In a preferred embodiment the extractor device is discarded. The extractor is self-contained and allows for a hygienic way of disposing of the used sample extractor. Upon undocking of the assay cartridge from the reservoir/extractor, the assay cartridge is inserted into the cartridge reader and set aside, or put into a purse where the assay develops (see, e.g., FIG. 1).

Figure 8B:
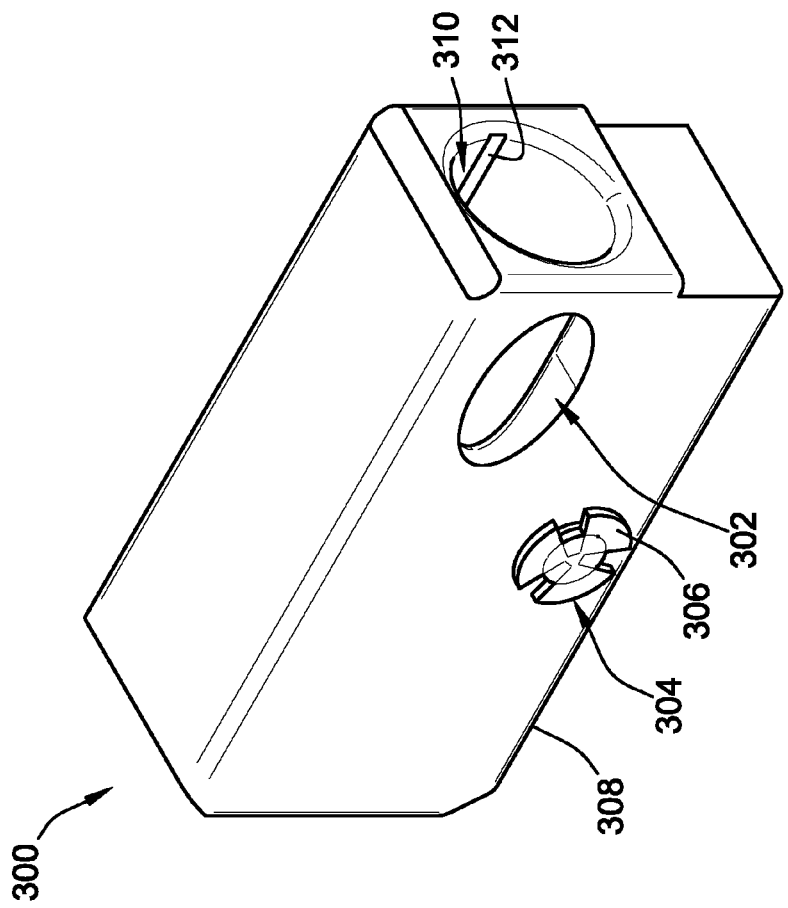
FIG. 8B is a back perspective view of the assay reader shown in FIG. 8A.
Figure 8A:
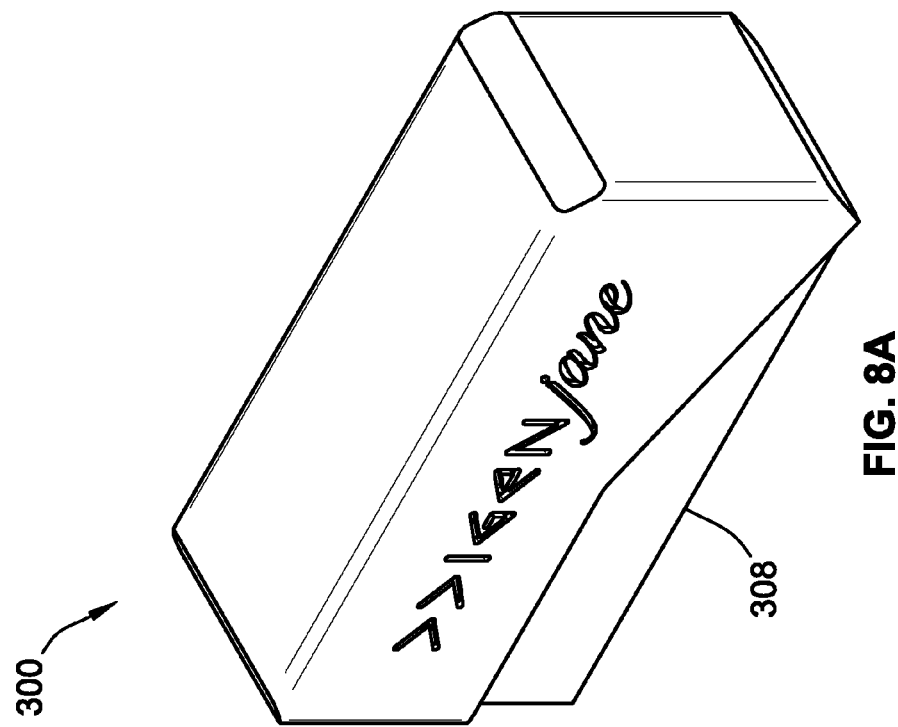
FIG. 8A is a front perspective view of an assay reader, in accordance with one exemplary embodiment.

In an embodiment shown in FIGS. 14A-14E, the assay cartridge 500 includes an internal assay reservoir 502, a plurality of assay slots 504, a docking end 506, a docking port 508, and a cartridge window 510. The docking end 506 is configured to be placed adjacent to and/or in contact with the top surface 612 of the extractor top 602, and the docking port 508 inserted within and in fluid communication with the fluid port 610. Biological fluid F from the extractor system 600 is transferred into the assay reservoir 502, from which the biological fluid F is further transmitted to one or more assays (located in the assay slots 504) to run desired tests and analysis. The results are displayed and/or viewed through the cartridge window 510. When the assay cartridge is inserted through the cartridge opening 300 of the assay reader 300 (shown in FIG. 8B), the cartridge window 510 is aligned with the reader window 302 for providing a clear viewing path to the camera 115 of the mobile phone 112 (which is attached to the assay reader 300 via the snap-on adapter 200).

In accordance with an alternative embodiment, the assay cartridge 500 includes a puncture apparatus (e.g., a needle) to connect to an extractor system for fluid extraction. In accordance with another alternative embodiment, the assay cartridge 500 includes a docking or luer lock system to connect to an extractor system. In accordance with yet another alternative embodiment, the assay cartridge 500 includes a reservoir that stores a small amount of extracted fluid (e.g., 100 microliters).

In other alternative embodiments, the assay cartridge 500 includes one or more buffers for sample processing. For example, the buffers include a buffer to dilute sample for minimizing background noise in the assay; a buffer with exogenous controls or spike-ins to normalize downstream data outputs; a buffer to preserve cells, DNA, RNA, or other biological components for analysis at a later date or to send a sample for analysis by experts; a buffer to extract particular biological components (e.g., DNA, RNA, proteins, etc.); a buffer to chemically remove particular biological components (e.g., $ZnSO_4$ to precipitate hemoglobin); a buffer to bind and remove particular biological components; a buffer housed in dissolvable or puncturable membrane; and/or a buffer that is free-floating.

In yet other alternative embodiments, the assay cartridge 500 has an assay chamber configured with multiple chamber slots to house one or more slots (e.g., similar to assay slots 504). Optionally, the assay chamber and a sample collection reservoir (e.g., the assay reservoir 502) are separated by a dissolvable membrane, a puncturable membrane, a chromatography plate for further filtration, and/or a porous filter to retain precipitated materials from a solution.

In another alternative embodiment, the assay chamber and the sample collection reservoir form a single chamber/reservoir, i.e., they are not separated. For example, if the sample is intended to be preserved and/or shipped to a referral laboratory, the assay cartridge 500 lacks an assay chamber, having only a sample collection reservoir. In such embodiments, the sample is sent to a CLIA laboratory where downstream analyses are performed on the biological sample collected. These downstream analyses include Enzyme-Linked Immunosorbent Assays and Next Generation sequencing such as DNA, RNA, microRNA, Methylome, strand-specific, and bacterial biome sequencing. Other downstream test may include, but are not limited to Mass Spectrometry, High Performance Liquid Chromatography, quantitative PCR, complete blood counts, proteomic analysis and small molecule analysis, cell and bacterial/viral cultures, and other informative analysis tools as needed for proper diagnosis of specific health conditions.

In yet other alternative embodiments, the assay cartridge 500 has electrodes for voltaic recording of electrochemical reactions and/or electrodes for passing a current through a test and to migrate a charge molecule (such as DNA, RNA, or protein). In yet another alternative embodiment, the assay cartridge 500 has electrodes to generate heat needed to catalyze a reaction.

4. Assays

The assay cartridge 500 is further configured to include various multiplexed assays, chemistries, assay reporter systems, lateral flow materials, and/or controls. The multiplexed assays include, by way of example, assays in series, which are likely to relay a more complete result than individual tests. Some exemplary multiplexed assays includes a rape test (e.g. PSA, ACP, and/or PEG), an STI test (e.g., gonorrhea and/or chlamydia), a cancer screening test (e.g., endometrial, cervical, fallopian tube, ovarian, uteran), a preterm birth test (e.g., pH, fFN, catehpsin-E), a fertility test (e.g., LH, FSH, AMH, TSH, progesterone), a nutrition and/or pre-pregnancy test (e.g., TSH, BPA, iron, folate, vitamin D), and/or other tests (e.g., PCOS, endometriosis). Some exemplary chemistries include a lateral flow chemistry, an isothermal PCR chemistry, a chemistry with DNA or RNA switches and gel electrophoresis, an aptamer-based amplification chemistry, and/or a voltaic enzyme linked assays chemistry.

The assay reporter systems of the assay cartridge 500 include, for example, a colorimetric-based or a chromogenic-based enzyme reporter. Optionally, configurations include colloidal gold and paramagnetic mono-dispersed latex particles. In alternative embodiments the assay reporter system includes a fluorogenic enzyme-based reporter, a dye-based report, an Atto 430-LS-based reporter, an Atto 465-based reporter, a brilliant violet 605-based reporter, a chromeo 494-based reporter, an alexa fluor 532-based reporter, an R-Phycoerythrin-based reporter, an SYBR-based reporter, a TAMRA-based reporter, a FAM-based reporter, and/or a voltaic reporter by enzyme catalysis of charged ions.

The lateral flow materials of the assay cartridge 500 include, for example, a hydrophilic surface with consistent flow rate; a highly regular surface, yielding cosmetically high-quality lines; a three-dimensional matrix with consistent pore size, thickness, and protein-binding capacity; and/or a true capillary flow with a variety of wicking rates. Some beneficial criteria of the lateral flow material include material thickness, with the desired criterion including having the material be as thin as reasonably possible; and material shelf-life, with the desired criterion including good fluid flow characteristics and/or low CVs for capillary rise time over its entire shelf-life (independent of treatment). Other examples of beneficial lateral flow materials include materials with minimal metal contaminants and/or low background fluorescence; materials that are stable in storage and/or are non-flammable; materials that can be activated for covalent linkage; materials with multiple functionality that can act as conjugate application area, a sample application area, a reaction surface, a separation medium, and a wick, all in one; and/or materials with a pore size in the range of about 8-15 microns.

The controls of the assay cartridge 500 include, for example, a series of controls to base algorithmic extrapolation of data to biologically relevant venous blood levels; internal controls to record a blood dilution factor; internal controls or standard dilutions to extrapolate concentrations of individual biomarker results; and/or external controls to normalize lot variations. In other embodiments, the controls includes controls to measure extent of hemolysis within a biological sample and/or controls to measure cell shearing within the biological sample.

In some embodiments, after the cervicovaginal fluid is in the assay cartridge, it comes in contact with diluents and reagents that are housed in dissolvable membranes or on test strips. The delayed release of these reagents is dependent upon the thickness of the dissolvable membranes when they come in contact with serum or cervicovaginal fluid. The membranes are housed in the upper portion of the assay cartridge, sealing the upper portion of the cartridge from the lower portion, where the test strips are housed. After the membranes are dissolved, cervicovaginal fluid plus reagents can flow down to the test strips for assay development. In some embodiments, the dissolvable membranes are made of an aqueous polymer matrix.

In some embodiments, the diluents and/or reagents are housed in a puncturable membrane. The puncturable membrane is punctured once the assay cartridge docks with and comes into fluid communication with the extractor. After the membrane is punctured, cervicovaginal fluid plus diluents and/or reagents flow down the test strips for assay development. In some embodiments, the puncturable membranes are made of a flexible polymer matrix.

The test strips are attached to plastic housings within the lower portion of the assay cartridge. In some embodiments, the test strips consist of nitrocellulose. In some embodiments, the test strips consist of Whatman® filter paper. In yet other embodiments, the test strips consist of other porous polymer materials suitable for biological processing with pre-designated wicking parameters. The first element of the test strips acts as a sponge and holds an excess of sample fluid. The fluid then migrates to the second element where conjugated reagent for detection of one or more specific analytes is in a dried format. After binding of analyte to the conjugated reagent, the sample/reagent complex then migrates to a portion of the strip where a capture molecule binds the complex. A time-released amplification solution is then released by the cartridge reader, and the resulting signal is amplified via a colorimetric amplification.

Several methods have been applied to the detection of pathogens and markers from clinical samples. These methods include, but are not limited to, conventional and real-time polymerase chain reaction (PCR), Isothermal PCR, restriction enzyme analysis, DNA, RNA, microRNA, methylome, and bacterial biome sequencing, DNA microarray analysis, flow cytometry, enzyme-linked immunosorbent assays ("ELISAs"), fluorescence in situ hybridization ("FISH"), and aptameric sensing platforms. PCR-based systems use consensus or degenerate primer sequences to allow for amplification and identification of DNA/RNA sequences associated with specific markers. ELISAs typically use antigens to detect the presence of specific antibodies that are made in response to infection, or antibodies that react with antigens, including markers of infection, disease or disorders.

In some embodiments, the assay uses existing rapid diagnostic technologies. The disclosed diagnostic tests use readily available and inexpensive materials (e.g., paper) and reagents (e.g., stable organic compounds, antibodies) to develop an immunoassay for the detection of analytes. The disclosed diagnostic tests can use direct, indirect, and sandwich assays on paper supports, gel electrophoresis based tests, PCR based isothermal tests (in vitro or in silico), and other oligo- and probe-based technologies, as well as electrochemical sensing technologies.

In some embodiments, the assay is paper-based. Paper provides a number of advantages over supports used in prior assays. For example, paper is commercially available, fabricated on a large scale all over the world, is widely abundant, inexpensive, biodegradable, renewable and allows for one-step functionalization (e.g., by periodate oxidation to form aldehyde-functionalized paper in wet solution or gas-phase silanization). The assays are also energy efficient, not requiring the use of pumps for liquids, as liquid wetting of the various components utilized is driven by capillary action. The assays do not require staining, instead allowing detection of analytes by more direct methods (e.g., direct visualization without the use of a stain). Because the support is paper, washing of the support is rapid and effective due to the large pore size of paper as compared to other supports, such as nylon membrane with smaller pores. The assays are flexible, allowing detection of both antigens (e.g., in direct, or sandwich methods) and antibodies (e.g., in indirect methods) as the analyte. Because of this flexibility, the disclosed diagnostics allow for detection of antigen or antibody analytes associated with any disease for which an antibody or antigen analyte is known (e.g., gonorrhea, chlamydia, HPV, etc.).

Paper supports useful in the assays include all types of cellulose materials that allow printing of wax-demarcated test zones. Wax printing requires two steps and produces hydrophobic barriers (for the test zones) that extend through the thickness of the paper. After wax printing, the paper is heated, and the wax melts and spreads vertically into the paper, creating the hydrophobic barrier needed to confine test reagents. Examples of useful paper supports include Whatman® filter papers, chromatography papers, polymeric-based membranes, and cotton or nylon fabric.

In some embodiments, the paper support is functionalized by oxidizing the surface with an oxidation agent to provide aldehyde-functionalized paper for antigen/antibody immobilization. In some embodiments, the paper is coated with agarose, which is then oxidized to provide the aldehyde functionalities useful for antigen/antibody immobilization. In some embodiments, the paper is coated with chitosan, which is then reacted with glutaraldehyde to provide the aldehyde functionalities useful for antigen/antibody immobilization. In some embodiments, multiple layers of antigen/antibody are prepared on the paper by alternatively adding antigen/antibody and glutaraldehyde on the paper. In some embodiments, the first layer of antigen/antibody is formed by using the original aldehyde functionalities present on the paper; followed by treatment with glutaraldehyde, which anchors the second layer to the first via cross-linking. In some embodiments, the exposed aldehyde functionalities are then reacted with an antigen or antibody to covalently bond these components to the paper support. In some embodiments, the unreacted aldehyde moieties are then blocked by treating the paper support with a non-reacting component (e.g., bovine serum albumin, casein, or ethanolamine) to provide a stable paper support ready to be shipped or used immediately in a diagnostic test.

In some embodiments, the assay uses functionalized antibodies. A functionalized antibody is an antibody with affinity for an analyte or another antibody which is functionalized with and coupled to a polymerization catalyst.

In a direct assay the antigen analyte is immobilized on the paper support and the paper support is subsequently treated with a primary antibody functionalized with a polymerization catalyst. In some embodiments, the antigen analyte is present in the clinical sample suspected of containing the antigen analyte, and the sample is contacted with the paper support. The primary antibody has affinity for and binds the antigen analyte and thereby becomes immobilized on the paper support through the antigen analyte. The paper support is then contacted with a monomer composition and exposed to a polymerization initiator, which initiates polymerization of the monomer composition on the areas of the paper support in proximity to the primary antibody functionalized with the polymerization catalyst. Unreacted monomer composition may then be washed away, leaving polymer only on areas of the paper support in proximity to the primary antibody and the antigen analyte.

Presence of the polymer, indicating the presence of the analyte, is then detected. Exemplary detection methods include, but are not limited to, direct visual observation, colorimetric readout, staining, pH change, scanning, and spectroscopic methods such as fluorescence, UV absorption or transmission.

An indirect assay is similar to the direct method, except it is used to detect an antibody analyte. An antigen having affinity for the primary (analyte) antibody is immobilized on the paper support. A species-specific secondary antibody having affinity for the primary (analyte) antibody is coupled to a polymerization catalyst. Accordingly, the antigen has affinity for and binds the primary (analyte) antibody, and the secondary antibody has affinity for and binds the primary antibody, both of which become immobilized on the paper support, the primary antibody immobilized through the antigen, and the secondary antibody immobilized through the primary antibody, which is in turn immobilized through the antigen. Accordingly, in some embodiments, the analyte is present in the clinical sample suspected of containing the analyte, and the sample is contacted with the paper support. As in the direct method, the paper support is then contacted with a monomer composition and exposed to a polymerization initiator, which initiates polymerization of the monomer composition on the areas of the paper support in proximity to the secondary antibody functionalized with the polymerization catalyst. Unreacted monomer composition may then be washed away, leaving polymer only on areas of the paper support in proximity to the secondary antibody, primary antibody, and the antigen. Presence of the polymer, indicating the presence of the analyte, is then detected. Exemplary detection methods are as disclosed above with respect to the direct method.

The sandwich method is similar to the direct and indirect methods, except a capture antibody is bound to the paper support in place of the antigen. The antigen analyte is then immobilized on the paper support through the capture antibody, and the paper support is subsequently treated with a secondary antibody functionalized with a polymerization catalyst. In some embodiments, the antigen analyte is present in the clinical sample suspected of containing the antigen analyte, and the sample is contacted with the paper support (which comprises the capture antibody). The secondary antibody has affinity for and binds the antigen analyte, becoming immobilized on the paper support through the antigen analyte and the capture antibody. The paper support is then contacted with a monomer composition and exposed to a polymerization initiator, which initiates polymerization of the monomer composition on the areas of the paper support in proximity to the secondary antibody functionalized with the polymerization catalyst. Unreacted monomer composition may then be washed away, leaving polymer only on areas of the paper support in proximity to the secondary antibody, antigen analyte and capture antibody.

Presence of the polymer, indicating the presence of the analyte, is then detected. Exemplary detection methods are as disclosed above with respect to the direct method.

The resultant polymer in turn becomes immobilized to the paper support, and can be clearly distinguished from polymers formed in bulk solution, which are easily washed away. Without wishing to be bound by theory, it is postulated that reaction of immobilized/activated radicals with radical species of the polymer in a termination step is responsible for the polymer immobilization phenomenon. Other mechanisms of polymer immobilization may involve some physical interactions between the polymer and the proteins on the surface, or interaction with paper support. In addition, in some embodiments the polymer is not soluble in water and so after attaching to the surface it cannot be washed away. In some embodiments, the polymer forms a hydrogel.

In some embodiments, the assays include (1) a paper support, (2) antibody functionalized with a polymerization catalyst, (3) a monomer composition capable of being polymerized in the presence of said polymerization catalyst, and (4) a polymerization initiator. In an exemplary assay, a clinical sample suspected of containing an analyte of interest is contacted either directly with the paper support (e.g., in a direct method) or to a paper support functionalized with an antigen having affinity for the primary (analyte) antibody (e.g., in an indirect method) or to a capture antibody having affinity for the antigen analyte (e.g., in a sandwich method) to immobilize at least a portion of the analyte, and unbound sample is removed by washing.

A functionalized antibody having affinity for the analyte of interest is then contacted with the resulting support, and excess functionalized antibody is removed by washing. The support is then treated with a monomer composition, and an initiator is introduced to induce polymerization via the polymerization catalyst. Polymerization results in hydrogel formation only in the areas of the support comprising bound analyte due to the fact that the polymerization catalyst is only present in these areas of the support due to the selective binding of the functionalized antibody to these areas. Unpolymerized monomer composition is removed by washing, and the analyte of interest can be detected by observing the areas of the support which comprise hydrogel, either directly (e.g., via a color change in the polymerized monomer composition in a colorimetric method) or indirectly (e.g., by various chemical, electrical, or spectroscopic methods well-known in the art, such as staining, scanning, fluorescence, UV absorption, magnetism, etc.).

In some embodiments, the assay is enzyme based, producing a time-dependent signal (i.e., producing a signal which changes over time). This type of assay requires test results to be recorded after a specific set time.

In a preferred embodiment, the assay is not enzyme based. This type of assay demonstrates improved stability over enzyme-based methods due to the lack of unstable enzymes. In some embodiments, the assay is based on gold-nanoparticle conjugated antibodies. Gold-nanoparticle-based assays in part eliminate the time-dependency problems of enzyme-linked antibody assays. This allows for signal amplification by polymerization to be conducted either immediately after capturing the antigen/antibody or at a later time, without affecting the diagnosis outcome. Notably, a typical assay according to the present disclosure is time-independent at a number of stages, providing for a flexible diagnostic method which can be readily prepared, shipped, and stored, and testing procedures which can be flexibly conducted without rigid adherence to time limits or storage conditions.

In some embodiments, the assay includes eosin as the polymerization catalyst and a tertiary amine co-initiator. Although eosin is oxygen-sensitive, the conditions and time scales of the assay overcome oxygen inhibition, allowing detection in an ambient environment (Kaastrup et al., Lab Chip 12:4055-4058; 2012). This is particularly useful in non-laboratory settings. This type of assay is specific (avoiding false positive results), sensitive (avoiding false negative results), user-friendly (simple to perform, using specimens obtained by non-invasive means), rapid, and deliverable (readily accessible to end users). This type of assay is low cost, fast, time-independent, sensitive and consistent.

An exemplary step-wise procedure for manufacturing an exemplary assay according to the present disclosure is depicted below:
1) react paper support with oxidizing agent to provide aldehyde-functionalized paper;
2) immobilize capture antibody on aldehyde-functionalized paper;
3) block unreacted aldehyde sites with non-reacting component;
4) treat paper support with sample suspected of containing analyte of interest;
5) wash paper support to remove unbound analyte;
6) treat paper support with functionalized antibody;
7) wash paper support to remove unbound functionalized antibody;
8) treat paper support with monomer composition;
9) expose paper support to stimulus to polymerize monomer composition in areas containing functionalized antibody bound to analyte;
10) wash to remove unpolymerized monomer composition; and
11) detect formation of the polymer formed in areas containing functionalized antibody bound to analyte.

As discussed herein, the items listed above can be categorized into three separate steps: (a) support preparation, steps 1-3; (b) analyte capture, steps 4-7; and (c) analyte detection, steps 8-11. After step 3 (block unreacted aldehyde sites with non-reacting component), a paper is produced which can be stored and shipped (for example, as part of a kit). The assay process can also be stopped indefinitely without risk of degradation of the components of the test after step 7 (wash paper support to remove unbound functionalized antibody). Further, in certain embodiments, the polymerization reaction is largely time-independent (i.e., the polymerization can precisely be turned "on" and "off" with the stimulus), meaning the time after which step 11 is carried out (i.e., detect formation of the polymer formed in areas containing functionalized antibody bound to analyte) is not critical to the results of the test. Notably, in some embodiments, eosin molecules immobilized on a support are capable of initiating polymerization after six months or more. In some embodiments, the time of the detection process (i.e., the initiation step) is short (about 60 seconds), in contrast with the time scale on the order of minutes for enzyme-based immunoassays. In some embodiments, the initiation step itself can be performed in less than 35 seconds. In some embodiments, the detection step can be effectively terminated (i.e., turned "on" or "off") by removing the light source, something which is not easily achieved in enzyme-linked immunoassays. In some embodiments, the development of the color used as readout is not dependent on the time between the taking of sample and initiating the assay; in other words, the color produced is stable with time.

In some embodiments, step 11 referenced above is achieved by adding phenolphthalein to the monomer composition. This assay mode is particularly useful under resource-limited settings, with no need for staining, scanning, or the use of spectroscopic methods. Phenolphthalein is colorless at a pH range of about 0 to less than 8.2, and does not affect the polymerization. Upon polymerization (step 9), the indicator is trapped in the polymer which in turn is immobilized on the paper support. Its color changes to pink upon the addition of a basic solution (for example, about 2 to about 6 µL, of about 0.01 to about 0.51 M NaOH), thus providing a visual photometric detection of the polymer, which in turn indicate the presence of analyte.

In one aspect, a method of detecting an analyte of interest in a clinical sample is disclosed, the method comprising (a) providing a paper support; (b) contacting the paper support with a sample, the paper support capturing at least a portion of any analyte present in the sample; (c) contacting the paper support with a first antibody; wherein the first antibody has affinity for and binds to the analyte; and wherein the first antibody comprises a polymerization catalyst; (d) contacting the paper support with a monomer composition; wherein the monomer composition comprises a monomer component capable of being polymerized in the presence of the polymerization catalyst; wherein at least a portion of the monomer component forms a polymer in the presence of the polymerization catalyst, resulting in a polymer; and wherein detecting the presence of the polymer indicates presence of the analyte.

In some embodiments, the method further comprises the step of (e) applying a polymerization initiator to the paper support, initiating polymerization in the presence of the polymerization catalyst.

In some embodiments, the method further comprises the step of (f) removing unpolymerized monomer composition from the paper support by washing with a first liquid. In some embodiments, the first liquid is deionized water.

In some embodiments, the monomer composition is adjusted or buffered to an appropriate pH. In some embodiments where the detection step requires a specific pH range, the monomer composition is adjusted or buffered appropriately to ensure this pH range is not reached until detection is desired. In some embodiments, the monomer composition comprises phenolphthalein, and the pH of the monomer composition is adjusted or buffered using an acid prior to the detection step. In some embodiments, the acid is hydrochloric acid.

In some embodiments, the paper support directly captures at least a portion of any analyte present in the sample. In other embodiments, the paper support is covalently bound to a capture antibody or antigen which has affinity for the analyte.

In some embodiments, the paper has affinity for the analyte and/or is not nitrocellulose.

In some embodiments, the capture antibody or antigen is covalently bound to the paper support by reacting the capture antibody or antigen with an aldehyde-functionalized paper to produce the paper support.

In some embodiments, the capture antibody or antigen is covalently bound to the paper support by reacting the capture antibody or antigen with an aldehyde-functionalized paper, followed by blocking unreacted aldehydes to produce the paper support. In some embodiments, the unreacted aldehydes are blocked with an agent selected from at least one of bovine serum albumin, casein and ethanolamine.

In some embodiments, the analyte is selected from an antigen and an antibody.

In some embodiments, the polymerization initiator is selected from the group consisting of at least one of light, heat, cooling, application of a magnetic field, application of an electrical field, application of electrical current, a chemical reagent and electricity. In some embodiments, the polymerization initiator is light. In some embodiments, the light comprises light having a wavelength of about 522 nm. In some embodiments, the polymerization initiator is light and the light is applied by way of a light box. In some embodiments, the light box comprises a timer. In some embodiments, the light source is an array of light-emitting diodes ("LEDs") with pulsing light at about 522 nm (about 30 mW/cm$^2$). In some embodiments, the light box applies light from above the paper support.

In some embodiments, the monomer composition further comprises an indicator. In some embodiments, the indicator is at least one of pH-sensitive, light-sensitive, temperature-sensitive, sensitive to electrical field or current, or sensitive to magnetic field. In some embodiments, the indicator comprises phenolphthalein and the method further comprises the step of treating the paper support with a base prior to detecting formation of the polymer. In some embodiments, the indicator comprises phenolphthalein.

In some embodiments, the detecting formation of the polymer comprises observing a color change mediated by phenolphthalein under basic conditions.

In some embodiments, the paper support is covalently bound to the capture antibody or antigen.

In some embodiments, the capture antibody or antigen is covalently bound to the paper support by reacting the capture antibody or antigen with an aldehyde-functionalized paper to produce the paper support.

In some embodiments, the capture antibody or antigen is covalently bound to the paper support by reacting the capture antibody or antigen with an aldehyde-functionalized paper, followed by blocking unreacted aldehydes to produce the paper support. In some embodiments, the unreacted aldehydes are blocked with an agent selected from at least one of bovine serum albumin, casein and ethanolamine.

In some embodiments, the assay is carried out by Loop Mediated Isothermal Polymerase Chain Reaction LAMP), which is a single tube technique for the amplification of DNA. LAMP is specifically beneficial over regular PCR in that it amplifies DNA and RNA target sequences at a constant temperature (60-65° C.) without sophisticated instrumentation. In LAMP, either two or three sets of primers and a polymerase with high strand displacement activity and replication activity are used to amplify target sequences.

In some embodiments the detection of amplification product through LAMP can be determined via photometry for turbidity caused by an increasing quantity of magnesium pyrophosphate precipitate in solution as a byproduct of amplification. This allows easy visualization by the naked eye. The reaction can be visualized either by measuring the turbidity or by fluorescence using intercalating dyes such as SYTO 9, or colorimetric dyes such as SYBR green. In-tube detection of DNA amplification is possible using manganese loaded calcein which starts fluorescing upon complexation of manganese by pyrophosphate during in vitro DNA synthesis.

In some embodiments, LAMP detection is paired with a set of DNA-based standards of known size and quantity in order to calculate an exact quantity of measured analyte, giving a quantitative readout.

In some embodiments, a paper filter is utilized with dry or encapsulated reagents in order to perform nucleic acid extraction and purification for downstream isothermal amplification of target sequence or analyte.

In some embodiments, the assay utilizes aptamer-sensing technologies for proteins and small molecule detection. Aptamers are single-stranded DNA/RNA oligonucleotides with characteristic 3D structures artificially selected from synthesized random-sequence nucleic acid libraries by in vitro evolution process called SELEX (Systematic Evolution of Ligands by Exponential Enrichment). Aptamers are able to bind their targets with high affinity and specificity, and they themselves by and large undergo the conformational transition that can be generally employed for designing analysis systems. Electrochemical aptameric assays are based on two signal transduction mechanisms: target binding-induced conformational change and strand displacement originating from competitive binding of target molecules with complementary oligonucleotides for recognition elements.

In some embodiments of aptamer-based assays the addition of gold nanoparticles, or other redox active moieties, mediators, enzymes, groove binders, or intercalators is used with modified electrode sensors. In the presence of target molecules are analytes, a detectable electrochemical signal can be generated and recorded for quantitative analysis of target analyte. Detection techniques can include cyclic voltammetry, differential pulse voltammetry, square wave voltammetry, anodic stripping voltammetry, chronopotentiaometric detection, and electrochemical impedance spectroscopy.

In some embodiments of aptamer-based assays, a fluorescent marker is used instead of electrochemical sensors, giving a fluorescent emission that can be imaged through a mobile device or external image capture device. This can be down using two methods. Aptamer-sensing assays can be converted to fluorescent sensors by either modification with fluorescent oligonucleotide analogs, or double-end-labeling with fluorescent marker and quencher. These systems allow for fluorescent emission upon conformation change of aptamer upon binding of target molecule or ligand.

In some embodiments, paper based assays are coupled with carbon ink or silver/silver chloride ink printed electrode sensors (a working electrode, a counter electrode, and a reference electrode). In this indirect detection method, target metal ions conjugates are detected by printed electrodes upon migration to electrode front using lateral flow and capillary action.

In some embodiments, the assays allow for the monitoring and/or diagnosis of a wide variety of biological analytes and diseases, and enable mass screening by a limited number of health professionals, as well as self-testing by patients at home (which can also be developed and analyzed later, upon arrival at a health care facility). The assays allow for detection of antigen, antibody, mineral, vitamin, hormone, or protein analytes present in semen, or associated with any disease, nutritive, or metabolic state for which an analyte, or with any disease, for which an antibody, antigen, mineral, vitamin, hormone, or protein analyte is known (e.g., gonorrhea, chlamydia, HPV, anemia, infertility, cancer, hypothyroidism, etc.).

5. Assay Reader

A small assay reader, for example the assay reader 110 shown in FIG. 1, is included in the first shipment of the testing kit. This assay reader is not disposable, and can be used repeatedly on a month-to-month basis. In some embodiments, the assay reader fits securely onto the headphone jack of a mobile device.

In some embodiments, the assay reader contains either rudimentary optics or the ability to hook up to available optics on the consumer's mobile device, and a small LED exposure light emitting a wide range of visual and hyperspectral wavelengths for colorimetric and fluorescent detection. In some embodiments, the assay cartridge slides into the assay reader and locks into place. Once the lock is engaged, an internal circuit begins a countdown to initiate the different steps in assay development. The circuit regulates the time of assay development and coordinates additional steps in the process of development and imaging of assay results. In a preferred embodiment, after the analytes have bound to conjugated reagents, the assay reader rotates a lever that punctures a small pouch containing polymer solution. The polymer solution covers the assay test strip. The reader then briefly turns on an LED light that initiates catalyzed amplification of polymer formation. Once polymerization has occurred, the reader sends a notification to the mobile device that the assay is ready for development. The user can then initiate development and reading of test results. In some embodiments, the development and reading of results is done through a button initiator on the reader itself. After the assay has developed, the assay reader takes a burst of images from the assay cartridge. In some embodiments, the development and reading of results is done through an app on the mobile device.

In some embodiments, the LED light is reflected through a series of mirrors that directs the light to the assay result portion of the inserted assay cartridge. This allows the light to illuminate the assay results in a directed fashion and illuminates the test results for the optics to record the image. Some embodiments have one or a series of LED lights housed within the reader to defract light at specific angles to record more accurate absorptions and/or fluorescence. The assay results are stored in the reader and can be transmitted to a mobile device to the user. Results can be transmitted from the reader to a mobile device or a computer through a cable connecting the reader to the device through the audio port of the mobile device. These images can be used to standardize and read each individual assay and can be subject to both binary and quantitative analysis for future assay implementation. The data can then be used to track the patient's health through the comprehensive mobile interface, or it can be sent via short-message service ("SMS") to designated health professionals for further testing and treatment.

In some embodiments, the assay reader attaches to an adapter that fits securely onto a mobile device, using existing optics of the mobile device. In other embodiments, the assay reader is a stand-alone device with internal optics. In yet other embodiments, the assay reader has built-in Bluetooth or wi-fi connectivity to relay data to a mobile device or computer. In other embodiments, the assay reader relays data to a mobile device or computer through a USB or other data transfer port.

In some embodiments, the results are recorded as an image. In other embodiments, the results are recorded by the light spectrum emitted by the colored result front, and a small optical spectrophotometer images the light spectrum emitted. In other embodiments, the results are recorded by voltmeter which senses a voltage change or a charge differential.

In an embodiment shown in FIGS. 8A-10B, the assay reader 300 is configured to connect with the snap-on adapter 200 and the camera 115 of the mobile phone 112, as discussed above in reference to FIGS. 5A-6E. In addition to the reader window 302, the reader latch 304, the latch inserts 306, and the bottom surface 308, the assay reader 300 also includes a cartridge opening 310 configured to receive and connect an assay cartridge 500 (shown in FIGS. 14A-14E).

The cartridge opening 310 includes an optional locating feature 312 configured to proper positioning and/or alignment of an assay cartridge within the assay reader 300. Optionally, the assay reader 300 lacks the reader window 302 (i.e., is a window-less assay reader).

The assay reader 300 is configured to attach to a mobile device, such as the mobile phone 112 to interface with optics, an audio port, or a power source from the mobile device to run, image, record, and/or transfer data from an assay received internally via an assay cartridge. In another embodiment, the assay reader 300 includes integrated optics, audio port, and/or power source to independently perform an analysis of the assay. For example, the assay reader 300 includes one or more lenses, sensors, filters, and/or voltaic electrodes to run and image assay test results.

Optionally, the assay reader 300 includes data recording. In some embodiments, assay test result data are recorded through a lens and sensor, with the lens being either internal or external and the sensor being configured to measure electromagnetic spectra in the visible or nonvisible spectra. The lens is configured to optically enhance a test image. By way of example, the sensor is a voltmeter that records charge differential. By way of a further example, the sensor records non-visual spectra or hyper spectral light wavelengths. The transmission of data occurs via one or more modes of communication including, for example wavelengths. In some embodiments, the sensor is a voltmeter. In some embodiments, the assay reader transmits data to a mobile device via a wired connection (e.g., an audio port adapter, a USB port, etc.) or a wireless connection (e.g., wi-fi, Bluetooth, etc.).

According to alternative embodiments, the assay reader 300 includes a filter, or a series of filters, configured to capture specific wavelengths. Optionally, the filter is configured to reduce noise generated by a respective assay.

According to other alternative embodiments, the assay reader 300 includes one or more automation features. For example, the assay reader 300 includes a mechanical lever to automate release of fluids, to puncture buffer membranes, and/or to initiate an initial catalyst of reaction. In another example, the assay reader 300 includes a basic relay of assay status to report to a mobile device and/or to initiate next steps, e.g., imaging. In yet another example, the assay reader 300 includes electrodes to connect to an assay cartridge and/or to initiate electric components, such as a voltmeter. The electrodes, by way of further example, initiate a charge to separate ions and charged molecules.

According yet other alternative embodiments, the assay reader 300 includes a light source. For example, the light source is a single light-emitting diode (LED) or a series of LEDs that are housed within the assay reader 300 to defract light at specific angles for recording absorptions and/or fluorescence with increased accuracy.

In some embodiments, the assay reader is an independent unit that does not associate with a mobile device. In these embodiments, the assay reader has its own power source or power adapter. Some embodiments contain lenses, sensors, filters, voltaic electrodes or any combination thereof to run and image assay results.

6. Snap-On Adapter

In an embodiment shown in FIGS. 5A-6E, a snap-on adapter 200 is configured for attaching an assay reader 300 (shown in FIGS. 8A-10C) to a mobile phone. The snap-on adapter 200 includes a top-left end 202, a top-right end 203, a bottom-left end 204, and a bottom-right end 205. Each of the ends 202-205 flexibly conforms to capture within an internal area a mobile phone (such as mobile phone 112 shown in FIG. 1), with an internal surface 206 of the snap-on adapter 200 being in contact with a front surface of the mobile phone 112 when the snap-on adapter 200 is attached to the mobile phone 112.

The snap-on adapter 200 further includes a viewing window 210, a reader interface 212, and a locating element 214. The viewing window 210 is in proximity to the top-left end 202 and is configured to rest over the camera 115 of the mobile phone 112. The viewing window 210 is further configured to align the camera 115 with a reader window 302 (shown in FIG. 8B) such that external light leaks are prevented or greatly reduced. The reader interface 212 is configured to receive a reader latch 304 of the assay reader 300 (shown in FIG. 8B) and facilitate the direct coupling of the snap-on adapter 200 and the assay cartridge 300. Specifically, the reader interface 212 has a three-pronged mating surface 218 with receiving holes 220 in-between each of the prongs for receiving respective latch inserts 306 of the reader latch 304.

The locating element 214 cooperates with the reader interface 212 to support a bottom surface 308 (shown in FIG. 9A) of the assay reader 300 and facilitate proper alignment and positioning of the assay reader 300 when the latch 304 is secured within the reader interface 212. To couple the snap-on adapter 200 and the assay reader 300, the two components are aligned such that the latch inserts 306 are initially aligned, respectively, with the receiving holes 220. Then, the snap-on adapter 200 and the assay reader 300 are rotated relative to each other to secure in place the latch inserts 306 relative and internal to the prongs of the three-pronged mating surface 218. The locating element 214 provides a stopping point for the rotation motion when the bottom surface 308 makes contact with a top surface of the locating element 214.

7. Mobile Interface

An interactive mobile app, such as the mobile app 112 illustrated in FIG. 1, ties data acquisition to comprehensive behavioral management. In an initial preferred embodiment the diagnostic assays focus on STIs, where the mobile app will track monthly results. In some embodiments, the individual user can detect the presence of semen in the cervicovaginal fluid sample. In some embodiments, the individual user can track therapeutic interventions as prescribed by primary care physicians to that particular user. Therapeutic options, safe sex options, and education are all aspects of the mobile app. In some embodiments, the app sources locations and clinics that tie into recommendation sites on the internet that help women make choices based on user verified and highly curated reviews/data.

In some embodiments the technology allows for assessment of pre-pregnancy health, including iron-deficiency, folate deficiency and vitamin optimization (ensuring a balance of all nutrients). A mobile app bundle can help women plan for pregnancy and healthy habits before, during, and after pregnancy.

In some embodiments, the individual user can detect and track, hormone levels, nutrition markers, fertility markers such as AMH, LH and FSH, shed reproductive cancer cells, reproductive disorders such as endometriosis and polycystic ovarian syndrome, environmental toxins, and other blood based or mucosa based health biomarkers.

A website and emailing list is optionally used to form a community of users who rely on the extraction device to keep them informed of relevant health issues. In some embodiments, the website is a bi-directional mechanism to engage with a target audience and provide education on health risks and factors.

In some embodiments, the website serves as a portal to collect phenotypic and demographic data on consumers. Lifestyle choices, predispositions for certain diseases, age, pre-existing conditions and other health factors determine what tests a woman should be testing for on a regular basis. User engagement with the website, such as what conditions she researches, user input on proprietary mobile applications, such as a pain diary, and responses to explicit questions help customize her experience and allow for personalized recommendations on test selection and frequency.

In some embodiments, proprietary algorithms determine her non-prescription based needs and offer to seamlessly facilitate buying and delivery of items such as food, consumables or OTC medications to her doorstep through integration with other vendors such as Amazon, Target, Walmart, Whole Foods and other retailers.

In some embodiments, proprietary algorithms determine appropriate support groups, on-line communities and other consumer introductions the user might want to access and be open to considering. The aggregate biological and phenotypic data provided by users facilitates a unique opportunity to connect clients with appropriate resources, groups and other users.

In accordance with alternative embodiments, the mobile app 112 further includes one or more automation protocols, secure data transmission features, data visualization features, and/or other functionalities. The automation protocols include, for example, a stored protocol or run parameters for lateral flow, isothermal PCR, aptamers, DNA/RNA switches, Voltage assays, and/or gel electrophoresis. In another example, for algorithm calculations, the automation protocols include imaging protocols for increased signal-to-noise ratios. In yet another example, the automation protocols includes actionable next-step protocols after results are reported. The next-step protocols include, for example, medical recommendations, health tips, nutrition suggestions, and/or purchasing on partner websites. In yet a further example, the automation protocols include curation protocols to external sites and/or partners for initiating next-step protocol recommendations.

The secure data transmission features include, for example, HIPPA compliance, anonymous log-in, identified log-in, de-identified data transmission, data encryption, and/or data transfer initiation to the cloud for storage and/or analysis. In another example, the secure data transmission features include transfer of data to medical personnel, a third-party insurer, and/or other group. In yet another example, the secure data transmission features include syncing with other health applications and/or services.

The data visualization features include, by way of example, visualization of data trends from month to month, and/or throughout the medical history of the respective patient or user. In another example, the data visualization includes a comparison of data to national and/or company averages. In yet another example, the data visualization includes charting of personal reference ranges and/or correlation discovery between different analyte trends.

Other functionalities include, by way of example, importing data from previous doctor visits, adding to data trends, recording all tests throughout a user's history, and importing old data from a storage facility (such as from the Cloud). According to other examples, functionalities include collection of third-party insurance information, including copays and cost structure of medical codes, and/or collection of medical personnel information.

Some exemplary embodiments of various aspects of the invention disclosed herein can be described by one or more of the following numbered paragraphs:

1. A medical kit for analysis of vaginal biological samples, the kit comprising:
    a sample collector insertable in a vaginal canal for collecting biological samples, the sample collector being compressible and including a cup-shaped head configured to cradle a cervix os;
    an extractor comprising
        a sample receptacle configured to receive the sample collector via an open end,
        a compression mechanism with a compression element and a release element, the compression element being movable inwards into the open end of the sample receptacle to apply a compression force in response to activation of the release element, and
        a filter which separates particles and components of biological fluid specific to the size of filter pores and is engaged upon activation of compression force, and
        a reservoir in fluid communication with the sample receptacle via the filter, the reservoir receiving the biological samples from the sample collector in response to the compression force being applied within the sample receptacle; and
    an assay cartridge with a docking mechanism configured to fluidly communicate with the reservoir of the extractor.
2. The medical kit of paragraph 1, wherein the sample collector comprises:
    an inner shell with a diffusely permeated thread matrix that facilitates collapse of the sample collector in response to a compressive force;
    an outer shell with a dense and absorbent plant fiber material; and
    a base with at least one layer of absorbent cotton material for forming a reinforced seal.
3. The medical kit of paragraph 1 or 2, wherein the sample collector comprises a material selected from a group consisting of a disposable material, a flushable material, a biodegradable material, an organic material, and a natural material.
4. The medical kit of any one of paragraphs 1-3, wherein the sample collector comprises a body connected to a removal element.
5. The medical kit of any one of paragraphs 1-4, wherein the compression mechanism comprises a spring, threaded screw, lever, or manual push syringe, coupled between the release element and the compression element, the spring, threaded screw, lever, or manual push syringe forcing the compression element inwards into the open end of the sample receptacle in response to the activation of the release element.
6. The medical kit of any one of paragraphs 1-5, wherein the filter is a removable filter.
7. The medical kit of any one of paragraphs 1-6, wherein the reservoir of the extractor comprises a plurality of detachable compartments, each detachable compartment of the plurality of detachable compartments being configured to receive a portion of the biological samples.
8. The medical kit of any one of paragraphs 1-7, wherein the extractor further comprises a filter having a plurality of pores and being selected from a group consisting of a cellulose filter, a plastic filter, a metal filter, and any combination thereof, wherein the filter is positioned between the sample receptacle and the reservoir.
9. The medical kit of any one of paragraphs 1-8, wherein the extractor further comprises a one-way pressure valve or resealable rubber slit, positioned within the reservoir, the pressure valve or rubber slit releasing biological samples collected in the reservoir in response to the docking mechanism of the assay cartridge being connected with the reservoir.
10. The medical kit of any one of paragraphs 1-9, wherein the assay cartridge comprises a viewing window for visualization of assay results.
11. The medical kit of any one of paragraphs 1-10, further comprising a cartridge reader comprising cartridge optics, a cartridge interface, and a mobile interface, the cartridge interface configured to receive the assay cartridge, the mobile interface being configured to communicate with a mobile device.
12. A method for home-care monitoring of a health condition, the method comprising:
    inserting a sample collector in a vaginal canal and collecting biological samples;
    removing the sample collector from the vaginal canal and placing the sample collector inside a sample receptacle of an extractor;
    compressing the sample collector within the sample receptacle by applying a force via a compression mechanism;
    eluting the biological material from the sample collector through a breakable buffer pouch;
    receiving the biological samples and buffer from the sample collector into a reservoir of the extractor;
    docking an assay cartridge in fluid communication with the reservoir, thereby allowing at least some of the biological samples to make contact with diluents or reagents of the assay cartridge; and
    determining a health condition based on a reaction between the biological samples and the diluents or reagents.
13. The method of paragraph 12, further comprising inserting the assay cartridge in a cartridge reader, the cartridge reader having internal circuitry for determining the health condition.
14. The method of paragraph 12 or 13, further comprising inserting the assay cartridge in a cartridge reader, the cartridge reader communicating data associated with the biological samples to an external device.
15. The method of any one of paragraphs 12-14, further comprising receiving health next-step instructions based on the determined health condition.
16. The method of any one of paragraphs 12-15, wherein the health condition is related to sexually transmitted infections (STIs), semen, cancer, fertility, or nutrient levels.
17. A medical kit for analysis of biological samples, the kit comprising:
    a sample collector insertable in a body cavity for collecting biological samples, the sample collector being compressible and including an absorbent-diffuse material for absorbing and releasing fluids;
    an extractor for acquiring the biological samples from the sample collector, the extractor including a receptacle in which the sample collector is received, the extractor including a compression mechanism for applying a force within the receptacle to release the biological samples from an inserted sample collector; the extractor including a breakable pouch of buffer or reagent to aid in elution of biological sample from sample collector;

an assay cartridge with an extractor interface and a reader interface, the extractor interface configured to be coupled in fluid communication with the extractor, the biological samples being transferred from the extractor to the assay cartridge via the extractor interface; and a cartridge reader with a cartridge interface configured for interfacing with the reader interface, the cartridge reader receiving assay data from the assay cartridge and communicating at least some of the assay data to a mobile device via a mobile interface.

18. The medical kit of paragraph 17, wherein the assay cartridge comprises internal circuitry configured to determine a health condition based on the biological samples.

19. The medical kit of paragraph 18, wherein the health condition is automatically determined without user intervention.

20. The medical kit of any one of paragraphs 17-19, wherein the assay cartridge comprises one or more readouts selected from a group consisting of a visual readout, a colorimetric readout, a fluorescent readout, a voltage readout, or a hyperspectral readout, the one or more readouts indicating the health condition.

21. The medical kit of any one of paragraphs 17-20, wherein the assay cartridge comprises a pouch with one or more reagents or buffers and the cartridge reader includes a puncture element, the pouch being punctured to release at least one of the one or more reagents or buffers in response to activation of the puncture element.

The disclosure is further illustrated by the following examples which should not be construed as limiting. The examples are illustrative only, and are not intended to limit, in any manner, any of the aspects described herein.

EXAMPLES

The following examples illustrate some embodiments and aspects of the invention. It will be apparent to those skilled in the relevant art that various modifications, additions, substitutions, and the like can be performed without altering the spirit or scope of the invention, and such modifications and variations are encompassed within the scope of the invention as defined in the claims which follow. The following examples do not in any way limit the invention.

The device as disclosed herein can be applied to the detection of a wide variety of infections, as it allows for detection of antigen or antibody analytes associated with any disease or disorder for which an antibody or antigen analyte is known, such as for a variety of STIs and cancers. The device can also be used to detect the presence of semen, identify genetic signatures and genomic material, as well as detect small molecules like environmental toxins such as BPA. In some embodiments, the device is used to assay for one of the following conditions. In some embodiments, the device is used to simultaneously assay for more than one of the following conditions using a single sample of cervicovaginal fluid. In some embodiments, the device is used to assay for more than one of the following conditions at different times using a single sample of cervicovaginal fluid. In some embodiments, the device is used to assay for more than one of the following conditions at different times using different samples of cervicovaginal fluid.

Example 1: Gonorrhea

Gonorrhea is an infection caused by the bacterium Neisseria gonorrhoeae. Transmission of this pathogen occurs during vaginal, oral, or anal sex (Moran, Clin. Evid. 200: 1604; 2007). While men often experience painful urination upon infection, women are mostly asymptomatic. If left untreated, gonorrhea can cause local disease such as pelvic inflammatory disease (PID), or can also affect other parts of the body, such as the joints and heart valves.

Traditionally, gonorrhea was diagnosed with gram stain and culture; however, newer PCR-based testing methods are becoming more common. The USPTF recommends screening for gonorrhea in women at increased risk of infection, which includes all sexually active women younger than 25 years (Meyers et al., Am. Fam. Physician 77:819-824; 2008). Screening for gonorrhea in women who are or intend to become pregnant, and who are found to be at high risk for sexually transmitted diseases, is recommended as part of prenatal care in the United States.

Past treatments for gonorrhea included a range of antibiotics, however, as of 2010, injectable ceftriaxone appears to be one of the few effective antibiotics, due to increasing rates of antibiotic resistance (Deguchi et al., J. Urol., 184:851-858; 2010).

In some embodiments, the disclosed device can be used to detect gonorrheal infections from menstrual blood or cervicovaginal fluids.

Example 2: Chlamydia

Chlamydial is a common STI that is caused by the bacterium Chlamydia trachomatis. Transmission occurs during vaginal, anal, or oral sex, but the bacterium can also be passed from an infected mother to her baby during vaginal childbirth. It is estimated that about 1 million individuals in the United States are infected with this bacterium, making chlamydia one of the most common STIs worldwide. Like gonorrhea, chlamydial infection is asymptomatic for a majority of women. If symptoms are present, they include unusual vaginal bleeding or discharge, pain in the abdomen, painful sexual intercourse, fever, painful urination or the urge to urinate more frequently than usual. Of those who develop asymptomatic infection, approximately half will develop PID. Infants born to mothers with chlamydia may suffer from pneumonia and conjunctivitis, which may lead to blindness. They may also be subject to spontaneous abortion or premature birth.

Diagnosis of chlamydial infection is usually done by nucleic acid amplification techniques, such as PCR, using samples collected from cervical swabs or urine specimens (Gaydos et al., J. Clin. Microbio., 42:3041-3045; 2004). Treatment involves various antibiotic regimens.

In some embodiments, the disclosed device can be used to detect chlamydial infections from menstrual blood or cervicovaginal fluids.

Example 3: Trichomoniasis

Trichomoniasis is considered the most common curable sexually transmitted disease. In the United States, an estimated 3.7 million people have the infection, but only about 30% develop any symptoms of the disease (Center for Disease Control fact sheet, 2015). In women, the most commonly infected part of the body is the lower genital tract. Nearly 70% of infections are asymptomatic. Not only can infection with Trichomonas increase one's risk of contracting and spreading other STIs, pregnant women with trichomoniasis are more likely to go into preterm labor, but also babies born to infected mothers are more likely to have officially low birth weight—less than 5.5 pounds (CDC fact sheet, 2015). Trichomoniasis can also lead to pelvice inflammatory disease, which may lead to infertility if untreated.

Diagnosis of Trichomoniasis includes a visit to the doctor's office, a physical exam, and sampling of vaginal secretions by a wet preparation test to visualize bacterial flagella present on the trichomonas bacteria (L. Campbell et al, Journal of Clincial Microbio, 2008). More recent technologies for diagnosis include rapid dipstick immunoassay and antigen tests directed at flagellar proteins of the bacteria. Treatment for Trichomoniasis is a one dose administration of an antibiotic, either metronidazole or tinidazole (CDC fact sheet, 2015).

In some embodiments, the disclosed device can be used to detect trichomoniasis infections from menstrual blood or cervicovaginal fluids.

Example 4: Syphilis

Syphilis is an STI that can cause long-term complications if not treated correctly. Symptoms in adults are divided into stages. These stages are primary, secondary, latent, and late syphilis. In pregnant women, having syphilis can lead to a low birth weight baby. It can also lead to delivering the baby too early or stillborn (CDC fact sheet, 2015).

Although *T pallidum* cannot be grown in culture, there are many tests for the direct and indirect diagnosis of syphilis. Still, there is no single optimal test. Direct diagnostic methods include the detection of *T pallidum* by microscopic examination of fluid or smears from lesions, histological examination of tissues or nucleic acid amplification methods such as polymerase chain reaction (PCR). Indirect diagnosis is based on serological tests for the detection of antibodies (Ratnam S, Can J Infect Dis Med Microbiol 2005). Treatment includes a single dose of intramuscular administration of penicillin (2.4 Million units).

In some embodiments, the disclosed device can be used to detect syphilis infections from menstrual blood or cervicovaginal fluids.

Example 5: Bacterial Vaginosis

Bacterial Vaginosis (BV) is an infection caused when too much of certain bacteria change the normal balance of bacteria in the vagina. Bacterial vaginosis (BV) is one of the most common lower genital tract conditions, occurring in 35% of women attending sexually transmitted infection (STI) clinics, 15% to 20% of pregnant women, and 5% to 15% of women attending gynecology clinics (Eschenbach D A, Am J Obstet Gynecol 1993). Pregnant women with BV are more likely to have babies who are born premature (early) or with low birth weight than women who do not have BV while pregnant. Low birth weight means having a baby that weighs less than 5.5 pounds at birth (CDC fact sheet, 2015).

Diagnosis of BV is typically done through a vaginal swab to assess the presence and balance of certain bacteria within the vaginal flora through PCR. A wet mount, whiff test, or pH test can also be performed in order to diagnose a possible bacterial infection.

In some embodiments, the disclosed device can be used to detect bacterial vaginosis from menstrual blood or cervicovaginal fluids.

Example 6: Pelvic Inflammatory Disease (PID)

Chronic and untreated infection with gonorrhea and chlamydia commonly leads to PID, a generic term for infection of the uterus, fallopian tubes, and/or ovaries. As the immune system tries to fight off the invading pathogens, it causes local inflammation and scarring. There are no tests for PID. A diagnosis is usually based on a combination of a patient's medical history, physical exam, and other test results. Since the most common causes of PID are gonorrhea and chlamydia, prevention of PID usually involves prompt diagnosis and treatment of these infections. However, since treatment of PID will not undo any damage that has already happened to one's reproductive system, successful treatment is heavily dependent on early diagnosis. Some patients may not realize they have PID because symptoms may be mild or nonexistent. However, if symptoms do exist, they include pain in the lower abdomen, fever, unusual discharge associated with odor, painful intercourse associated with bleeding, burning sensation during urination, or bleeding between periods. Women who have had a history of PID are more likely to have a diagnosis of endometriosis. Consequently, they are also more likely to be in need of a hysterectomy, have an ectopic pregnancy or suffer from infertility.

In a preferred embodiment, the disclosed device focuses on detecting gonorrheal and chlamydial infections from menstrual blood or cervicovaginal fluids, and includes the ability to send results to a physician, educate on safe sex practice and available interventions/therapeutics. It also includes the ability to track monthly results and options for coping and dealing with STIs.

Example 7: Endometriosis

Endometriosis is a gynecological condition in which cells from the lining of the uterus (endometrium) appear and flourish outside the uterine cavity, most commonly on the membrane which lines the abdominal cavity, the peritoneum. Although the exact cause of endometriosis is not certain, there are several possible explanations, such as retrograde menstruation, surgical scar implantation, immune disorders, as well as heredity. Significantly, there is an established association between endometriosis and infertility (Buletti et al., J. Assist Reprod. Genet. 27:441-447; 2010). Current diagnostic methods for endometriosis involve a laparoscopy, an invasive surgical procedure. There is no cure for endometriosis, but it can be treated in a variety of ways, including with pain medication, hormonal drugs, and surgery.

In some embodiments the disclosed device focuses on detecting markers associated with endometriosis from menstrual blood or cervicovaginal fluids. This embodiment allows women to identify and track staging of the disease and helps them navigate therapeutic options such as hormonal therapy, nonsteroidal anti-inflammatory drugs ("NSAIDs") and surgery.

Example 8: Polycystic Ovarian Syndrome and Ovarian Reserve

Antimüllerian hormone (AMH) is produced in the adult female exclusively by granulosa cells, declines with age, and is widely considered a highly sensitive marker of ovarian reserve. Serum AMH level is increased significantly more in women with polycystic ovary syndrome (PCOS).

Serum AMH level seems to be related to the severity of PCOS and correlates with its clinical diagnostic hallmarks, including hyperandrogenism, oligo/anovulation and polycystic ovarian morphology. AMH level may also be associated with qualitative assisted reproductive technology outcomes such as pregnancy and live birth rates inde-pendent of age (Tal R, et al, Amer J of OB & GYN, 2014).

The current method of evaluating a women's AMH level is through Enzyme Linked Immuno-Sorbedent Assay (ELISA), and is performed on blood serum. This test provides an absolute quantification of the amount of AMH circulating in the blood.

In some embodiments the disclosed device focuses on diagnosing or assessing risk of PCOS and ovarian reserve from menstrual blood or cervicovaginal fluids.

Example 9: Human Papillomavirus (HPV) Infection

Human genital papillomaviruses are amongst the most prevalent sexually transmitted human pathogens. Most genital HPV infections in women produce transient squamous cell abnormalities of the cervix that resolve completely, and so the probability of any one HPV infection progressing to cervical cancer is quite small. Nevertheless, HPV infection is a cause of nearly all cases of cervical cancer (Lynge et al., APMIS 122:667-673; 2014). Persistent infections increase the risk of precancerous lesions, which can progress to invasive cancer. Progression to invasive cancer can be prevented when subclinical HPV infection is detected early and regular examinations are performed.

The Pap smear is the current gold standard for the detection of HPV infection. Pap smears have reduced the incidence and fatalities of cervical cancer in the developed world; however, the USPTF now recommends Pap smears only every three years. Recently developed HPV vaccines (Cervarix and Gardasil), which prevent infection with HPV types 6, 11, 16, and 18, may lead to further decreases. However, these vaccines are currently only recommended for women age 25 or younger.

In some embodiments, the disclosed device can be used to detect HPV infections from menstrual blood or cervicovaginal fluids.

Example 10: Yeast Infection

Vaginitis is one of the most common complaints for physician visits in the United States (Paavon J, et al, Infec Dis Clin North Am 1987) that results in 10 million office visits per year (Sparsk J M, J Reprod Med, 1991). 30% of all vaginitis cases are caused by infection with Candida species commonly referred to as yeast infections. Untreated vaginal candidiasis in pregnant women can result in passing the infection to the baby during delivery and the development of oral thrush in the newborn.

Current recommended guidelines regarding screening for Candida, as published by the Centers for Disease Control and Prevention (CDC) in 2004, consist of microscopy, saline wet mount, whiff test, pH determination, or gram stain. More current diagnostic tools include rapid dipstick antigen test. Treatment for yeast infections is now available over the counter and includes oral administration as well as topical lotions. Probiotic treatment has also been shown to be affective in reestablishing vaginal flora to help treat and prevent yeast infections.

Although candidiasis can occur without any identifiable precipitating factor, certain conditions that disrupt the balance of normal vaginal flora can predispose women to the development of symptomatic infection. The use of antibiotics, oral contraceptive pills, contraceptive devices, high estrogen levels (as during pregnancy and hormone replacement therapy), or certain medical conditions such as uncontrolled diabetes mellitus and HIV can increase an individual's risk of the development of candidiasis (Sparsk J M, J Reprod Med, 1991).

In some embodiments, the disclosed device can be used to detect candidiasis based yeast infections from menstrual blood or cervicovaginal fluids.

Example 11: Fetal Trophoblasts

Trophoblast cells have been picked up in transcervical retrieval methods such as cervical lavage and brushing. These cells have a wealth of information that can be interrogated for data on the health of the fetus.

Gender identification Prior to 13-15 weeks of gestation, it is believed that small areas of erosions allow trophoblast cells to cross the decidua capillaries and reach the uterine cavity (Imudia, 2010). These of fetus Using a Y chromosome antibody, fetal trophoblast cells can be assayed for the presence or absence of Y chromosome DNA to uncover, at very early stages, the sex of the fetus.

Imudia et al. states that changes in the amount of fetal trophoblasts cells can be indicative of abnormal pregnancy. For example, a dramatic reduction of trophoblasts in cervical secretions is indicative of an ectopic pregnancy, as the fetal trophoblast do not enter into the uterine cavity (Imudia, 2010).

HLA-G is a fetal specific protein associate with fetal trophoblast and can be used to quantify the amount or relative number of trophoblasts present in a sample. Quantification of HLA-G as a proxy for trophoblast quantity could allow for the detection of abnormal preganancies such as ectopic and molar pregnancies.

In some embodiments, the disclosed device can be used to detect health of fetus and pregnancy through monitoring trophoblasts, assessing trophoblasts for development abnormalities and sex determination, and quantifying number of trophoblasts from cervicovaginal fluids.

Example 12: HIV and CD4 Monitoring

According to the CDC, at the end of 2011, 23% of all people living with HIV in the United States were women. Not all US women who are living with HIV are getting the care they need. Of all women living with HIV in 2011, only 45% were engaged in care, and only 32% had achieved viral suppression (CDC Fact Sheet, 2015).

The risk of getting HIV during vaginal sex without a condom is much higher for women than it is for men. Women who have been sexually abused may be more likely than women with no abuse history to engage in sexual behaviors like exchanging sex for drugs, having multiple partners, or having sex with a partner who is physically abusive when asked to use a condom.

Diagnosis of the disease can occur at your doctors office either through a blood test for either the virus or antibodies for the virus (either polymerase chain reaction or immunoassay). A rapid test is also available, both point-of-care and over-the-counter. Treatment includes a lifelong regiment of antiretroviral drugs. If HIV infection is suspected, a course of antiretroviral drugs can given up to 72 hours after the potential exposure and greatly reduces one's risk of contracting the disease. This therapy is known as Post Exposure Prophylaxis, or simply PEP.

Once an individual tests positive, regular doctor's visits are needed to test for the total number of T4 immune cells that are found in the blood. This particular cell type is the target for HIV infection and a low level of T4 cells is indicative of advanced disease. Therefore, constant monitoring is needed to assess therapeutic effectiveness and progression of the disease. Currently this is done in the laboratory through a process call flow cytometry. However more rapid tests are currently being developed, including the potential for a later flow, semi-quantitative dipstick test that will test for CD4 cells.

In some embodiments, the disclosed device can be used to detect HIV infection and monitor CD4 cell counts in menstrual blood or cervicovaginal fluids.

Example 13: Preterm Birth and Recurrent Pregnancy Loss

Preterm delivery and recurrent pregnancy loss are some of the most challenging problems in obstetrics to date, and the diagnosis of preterm labor is often innacurate (Leitich, 1999). Normal and preterm birth is initiated through a cascade of physical and enzymatic changes that prepare the reproductive system to begin the birthing process (Quinzio, 2007). A key marker that can be used to determine a women's risk of preterm labor is the presence of fetal fibronectin (fFN) between 24-34 weeks in vaginal secretion. fFN plays an important role in securing the fetal sac to the uterine lining.

During early pregnancy, fFN is shed into the cervical matrix at high amounts as the fetus implants and secures into the uterine wall. In normal pregnancy, the levels of fFN dramatically drop until late in pregnancy as the fetus prepares for the birthing process and the adhesion of the fetal sac to the uterine wall begins to degrade. However, in preterm labor, fFN can be detected in weeks 24-34 as the adhesion between the fetal sac and uterine wall begin to prematurely degrade.

fFN is therefore used, and is available as a rapid lateral flow assay, to determine a women's risk of preterm labor. If caught early, administration of progesterone can help to prevent further degradation of the adhesion interface of the fetal sac and uterine wall, thus improving a women's chance of carrying the fetus to term (da Fonseca, 2002). Currently this test is performed in the clinic, where a cervical spungeis inserted into the vaginal canal, and placed against the cervical os to collect cervical fluid. This cervical fluid is then assayed for the presence of fFN. Other tests such as IL-6, PAMG-1, and IGFB are other similar immunotest that are utilized in some clinics to assess a women's imminent risk of preterm delivery.

Another marker that is used to determine the onset of the birthing process and risk of preterm labor is a change in pH of vaginal secretions due to the introduction of amniotic fluid as it begins to leak from the fetal sac before rupture. This pH change can increase the overall pH of the vagina from a normal range for 4.5-6 to a pH reading over 7. Currently a rapid pH test, known as a nitrazine stick, can be used to assess the pH of the vaginal canal to determine if amniotic leakage has occurred and can be used as a proxy for impending labor.

Both fFN and Nitrazine can be leveraged to assess a women's risk of preterm labor and provide actionable steps with a physician to treat the condition and improve preterm labor outcomes.

In some embodiments, the disclosed device can be used to detect and monitor preterm birth risk and recurrent pregnancy loss risk within cervicovaginal fluids.

Example 14: Breast Cancer

Signs of breast cancer may include a lump in the breast, a change in breast shape, dimpling of the skin, fluid coming from the nipple, or a red scaly patch of skin. In those patients exhibiting metastasis, there may be bone pain, swollen lymph nodes, shortness of breath, or yellow skin. Age and sex are the two primary risk factors for breast cancer. Other risk factors include obesity, lack of physical exercise, alcohol consumption, hormone replacement therapy during menopause, ionizing radiation, early age at first menstruation, and having children late or not at all. A small minority of breast cancer cases are due to genes inherited from a person's parents, including BRCA1 and BRCA2 among others.

Current methods of breast cancer screening include clinical and self breast exams, mammography, genetic screening, ultrasound, and magnetic resonance imaging. The USPTF recommends mammography every two years in women between the ages of 50 and 74. The risks of more frequent mammograms include a small but significant increase in breast cancer induced by radiation.

Most breast cancer cases are discovered when the woman feels a lump in her breast. Lumps found in lymph nodes located in the armpits can also indicate the presence of breast cancer. However, currently, the earliest breast cancers are detected by a mammogram. Even so, most symptoms of breast disorders, including most lumps, do not turn out to represent underlying breast cancer, and in fact, fewer than 20% of lumps are cancerous.

Treatment of breast cancer usually involves a combination of surgery, radiation and chemotherapy. In some embodiments the disclosed device focuses on detecting markers associated with breast cancer from menstrual blood or cervicovaginal fluids. This embodiment allows women to identify and track staging of the disease and helps them navigate therapeutic options such as hormonal therapy, NSAIDs and surgery.

Example 15: Ovarian Cancer

There are often no early signs of ovarian cancer. Later symptoms include bloating, pelvic pain, and abdominal swelling, among others. Ovarian cancer occurs more frequently in women who ovulate more, therefore, those who never have children are at increased risk. Other risk factors include hormone therapy after menopause, use of fertility medication, smoking, and obesity. Factors that decrease the risk include hormonal birth control, tubal ligation, and breast feeding. About 10% of cases are hereditary and those with the gene mutations BRCA1 and BRCA2 have an approximately 50% risk of developing the disease. Ovarian carcinomas are the most common type of ovarian cancer, making up more than 95% of cases. They include five main subtypes, of which high-grade serous carcinoma is most common. These tumors are believed to usually start from the cells covering the ovaries, though some may form from the fallopian tubes (Piek et al., Adv. Exp. Med. Biol. 622:79-87; 2008). Less common types of ovarian cancer include germ cell tumors and sex cord stromal tumors.

Diagnosis of ovarian cancer starts with a physical examination (including a pelvic examination), a blood test (for CA-125 and sometimes other markers) and a transvaginal ultrasound. The diagnosis is confirmed by examination of a biopsy usually removed during surgery. If treated, early ovarian cancer may be curable. Treatments often include some combination of surgery, radiation therapy and chemotherapy.

Central to the application of the disclosed device is the identification of markers for ovarian cancer, including circulating and shed tumor cells. Ovarian cancer is curable if detected and treated early enough, however, signs of the disease are absent in the early stages. Many of the symptoms are also non-specific (bloating, pelvic pain, etc.) and therefore difficult for a woman to disambiguate.

As a result, diagnosis often occurs in stages III/IV of the cancer. The literature points to multiple markers, such as CA-125, serum alpha-fetoprotein and lactate dehydrogenase ("LDH"), which can offer insight into diagnosis (Chudecka-Glaz et al., J. Ovarian Res. Epub; 2014; Jashnani et al., Indian J. Pathol. Microbiol. 56:54-56; 2013). Given the especially silent nature of ovarian cancer, a sentinel system optimized for constant surveillance is particularly germane to improve overall outcome of the disease.

In some embodiments the disclosed device focuses on detecting markers associated with ovarian cancer from menstrual blood or cervicovaginal fluids.

Example 16: Cervical Cancer

More than 90% of cervical cancer cases occur as a result of HPV infection. Most people who have had HPV infections, however, do not develop cervical cancer (Robbins Basic Pathology ($8^{th}$ ed.) pp. 718-721). Other risk factors for cervical cancer include smoking, immunosuppression, use of hormonal birth control pills, and early onset of sexual activity coupled with having multiple sexual partners. Early in infection there are typically no symptoms. Later symptoms may include abnormal vaginal bleeding, pelvic pain or pain during sex. Diagnosis typically occurs by cervical screening with Pap smears followed by a biopsy. Medical imaging is then done to determine whether or not the cancer has spread.

Cervical cancer screening using the Pap smear or acetic acid can identify precancerous changes which when treated can prevent the development of cancer. Treatment of cervical cancer may consist of some combination of surgery, chemotherapy and radiotherapy.

In some embodiments the disclosed device focuses on detecting markers associated with cervical cancer from menstrual blood or cervicovaginal fluid.

Example 17: Uterine or Endometrial Cancer

Uterine or Endometrial cancer is both the most common type of uterine cancer and the most common cancer of the female reproductive system, accounting for approximately 6 percent of all cancers in women in the United States (National Cancer Institute). Most uterine cancers start in the endometrium (the inner lining of the uterus). This is called endometrial cancer. Most endometrial cancers are adenocarcinomas (cancers that begin in cells that make mucus and other fluids). The most common sign of endometrial cancer is unusual vaginal bleeding. Since 2002, overall incidence rates have not changed significantly, whereas mortality rates have been slowly rising since 2001 (National Cancer Institute). Although the incidence rate of endometrial cancer is only slightly higher in African American women than in whites, the mortality rate of African American women is nearly twice as high as that of all other racial/ethnic groups.

Diagnosis for endometrial cancer is down either through an endometrial biopsy, through a procedure known as a dilatation and curettage—a procedure used to remove tissue from inner lining of the uterus, through physical exams and transvaginal ultrasound, or a CT scan. Because endometrial cancer begins inside the uterus, it does not usually show up in the results of a Pap test. For this reason, a sample of endometrial tissue must be removed and checked under a microscope to look for cancer cells. A recent genomic study characterized nearly 400-endometrial tumors identified molecular signatures specific to endometrial cancer (CGASN, 2013). This work allows for future characterization of endometrial tumors for possible screening and more advanced diagnostics.

Uterine cancer is treated by one or a combination of treatments, including surgery, radiation therapy, chemotherapy, and hormone therapy. Combinations of treatments are often recommended. Surgery can include partial or full hysterectomy. Often the stage of cancer determines the specific combination of therapy.

In some embodiments the disclosed device focuses on detecting markers associated with uterine or endometrial cancers from menstrual blood or cervicovaginal fluid.

Example 18: Pre-Pregnancy Nutrition

It has been shown that many vitamins and minerals are essential for healthy pregnancy. For example, low maternal folate levels are associated with allergy sensitization and asthma (Lin J et al, J Allergy Clin Immunol, 2013). Low maternal iron levels have been associated with lower mental development (Chang S. et al, Pediatrics, 2013), and low iron may even increase a mother's risk of post-partum depression. Vitamin B12, which is essential for red blood cell formation, is essential for pregnant women and the health of their fetus. Folate, Iron, and Vitamin B12 can all cause anemia and increase a pregnant woman's risk of preterm labor, developmental delays of the child, as well as neural tube defects during development. Based on a WHO review of nationally representative samples from 1993 to 2005, 42 percent of pregnant women have anemia. Other essential vitamins and minerals that promote a healthy pregnancy are well validated and include Vitamins A, D, E, Other B Vitamins, Calcium, and Zinc.

In some embodiments the disclosed device focuses on detecting levels of vitamins and minerals from menstrual blood or cervicovaginal fluid that will help maintain healthy levels within the body for pregnancy.

Example 19: Hormones—Metabolism

The thyroid gland is primarily involved in the control of metabolism. Abnormal thyroid function directly and indirectly affects reproduction as well. Infertility and adverse pregnancy outcomes are more common when the thyroid gland is hypo- or hyperactive. Higher miscarriage rate, more frequent preterm deliveries, increased hypertension, diabetic complications, higher risk for placental abruption, and adverse fetal effects have all been reported with thyroid dysfunction in pregnancy. At least half of implanted embryos will not survive to delivery, and on average 20% of clinical pregnancies are lost (Schwartz N. et al, J Clin Enocrinol Metab. 2010).

During pregnancy, a 30%-40% increased need for thyroid hormones is the result of increased placental uptake, higher thyroid-binding globulin levels, and greater blood volume (Schwartz N. et al, J Clin Enocrinol Metab. 2010). Those with subclinical hypothyroidism and/or high-normal TSH levels at the beginning of pregnancy may not be able to meet these needs and may show signs of thyroid insufficiency during pregnancy.

Women with thyroid disease visit clinicians 2-4 times per year to check for thyroid hormone levels to adjust medications. And before pregnancy, regular monitoring of thyroid hormone and treatment could be an effective way of maintaining healthy TSH levels during pregnancy.

In some embodiments the disclosed device focuses on detecting levels of thyroid stimulating hormone from menstrual blood or cervicovaginal fluid.

Example 20: Hormones—Fertility and Menapause

Fertility—Progesterone is one of the most important hormones for pregnancy with myriad functions from ensuring implantation of the egg into a healthy uterine wall, to ensuring embryo survival and prevention of immune rejection of the developing baby. Many other hormones act in concert with progesterone, like Follicular Stimulating Hormone (FSH) and Luteinizing Hormone (LH) and can be used to assess optimal fertility windows on a monthly basis. And in fact an over dominate production of estrogen can lead to progesterone deficiency and thus difficulty getting or staying pregnant. It is important that women not only monitor FSH and LH to determine optimal fertility for getting pregnant, but insure that sufficient levels or progesterone are being produced to insure pregnancy and viability of the fetus. A study from the British Medical Journal, 2012, demonstrated that a single progesterone level test could help discriminate between viable and nonviable pregnancies. Among women who had an ultrasound, 73 percent had nonviable pregnancies. But among women with progesterone levels below 3 to 6 nanograms per milliliter, the probability of a nonviable pregnancy rose to more than 99 percent (Gallos L et al. British Medical J, 2012).

Perimenapause—Monitoring hormone levels during the menopausal transition may help women better understand important changes in their body and allow them to make more informed decisions about health, diet, and lifestyle. According to Hale GE (Best Pract Res Clin Obstet Gynaecol, 2009) data from endocrine studies on women throughout the menopausal transition show changes in levels of steroid hormones and gonadotrophins, (Progesterone, Estrodiol, LH, FSH and AMH) and established that follicle-stimulating hormone undergoes the first detectable change while menstrual cycles remain regular. Erratic and less predictable changes in steroid hormones follow, especially with the onset of irregular cycles. Later serum hormone studies on the inhibins and anti-Mullerian hormone established that diminishing ovarian follicle number contributes to the endocrine changes with advancing reproductive age.

Many fertility issues revolve around genetic, anatomical or other disorders that may either prevent a woman from becoming pregnant and/or staying pregnant. Some of these disorders include hormonal imbalances, diabetes, a short or insufficient cervix, and acute or chronic infections. A cascade of genes has been implicated in the occurrence of getting and staying pregnant. These genes have been studied using genotyping, gene expression, and proteomic analysis to assess a woman's ability to stay pregnant.

In some embodiments the disclosed device focuses on detecting levels of Progesterone, LH, FSH, Estrodiol, AMH, genotyping, gene expression through RNA and methylome sequencing, qPCR and proteomic analysis for fertility and menopause management from menstrual blood or cervicovaginal fluid.

Example 21: Environmental Toxins

There is growing evidence that bisphenol A (BPA) may adversely affect humans. BPA is an endocrine disruptor that has been shown to be harmful in laboratory animal studies. As reported by Rochester J (Reproductive Toxicology, 2013) BPA has been shown to affect many endpoints of fertility, including poor ovarian response, viability of oocytes, and reduced yield of viable oocytes. BPA has also been correlated with PCOS, endometrial disorders, an increased rate of miscarriages, premature delivery, and lower birth weights.

Current methods of detecting BPA in blood are done through mass spectrometry. Monitoring of BPA levels in blood may help reduce or eliminate certain sources of BPA in a women's environment, aiding in overall health.

In some embodiments the disclosed device focuses on detecting levels of BPA toxin from menstrual blood or cervicovaginal fluid.

Example 22: Alcohol Abuse

Clinicians can use several biochemical measurements to objectively assess patients' current or past alcohol use. Several more experimental markers hold promise for measuring acute alcohol consumption and relapse. These include certain alcohol byproducts, such as acetaldehyde, ethyl glucuronide (EtG), and fatty acid ethyl esters (FAEE), as well as two measures of sialic acid, a carbohydrate that appears to be altered in alcoholics (Peterson K, Alcohol Research and Health, 2005). Clinicians have had access to a group of biomarkers that indicate a person's alcohol intake. Several of these reflect the activity of certain liver enzymes: serum gamma-glutamyltransferase (GGT), aspartate aminotransferase (AST), alanine aminotransferase (ALT), and carbohydrate-deficient transferrin (CDT), a protein that has received much attention in recent years. Another marker, N-acetyl-β-hexosaminidase (beta-Hex), indicates that liver cells, as well as other cells, have been breaking down carbohydrates, which are found in great numbers in alcohol (Javors and Johnson 2003).

In some embodiments the disclosed device focuses on detecting markers associated with alcohol abuse from menstrual blood or cervicovaginal fluid.

Example 23: Semen Exposure

In many cases of sexual assault, traces of semen are left behind in the vagina, allowing for later collection and analysis. Semen consists of a variety of proteins, vitamins, nutrients, blood group antigens, and DNA. The preservation and/or analysis of semen can facilitate later development of a DNA profile. In some embodiments, the disclosed kit allows for at-home detection of analytes from semen.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

Each of these embodiments and obvious variations thereof is contemplated as falling within the spirit and scope of the claimed invention, which is set forth in the following claims. Moreover, the present concepts expressly include any and all combinations and sub-combinations of the preceding elements and aspects.

What is claimed is:

1. A system for extracting and preserving components of a biological sample of a subject in their original state, comprising:
   a sample collector that non-invasively collects said biological sample from a vaginal canal of said subject, wherein said sample collector collects and retains said biological sample from said vaginal canal;
   an extractor comprising (i) a sample receptacle that receives said sample collector via an opening, (ii) a breakable buffer pouch comprising a buffer for preserving said components of said biological sample in their original state during storage or shipping of said biological sample for subsequent processing or analysis of said biological sample, wherein said breakable buffer pouch is separate from said sample receptacle and configured to release said buffer to contact said sample collector in said sample receptacle when said breakable buffer pouch is broken, and (iii) a collection reservoir that is in fluid communication with each of said sample receptacle and said breakable buffer pouch when said breakable buffer pouch is broken, wherein said collection reservoir receives a solution, said solution comprising said buffer from said breakable buffer pouch and said biological sample from said sample receptacle, when said sample collector is in said sample receptacle, wherein said collection reservoir is separate from said sample receptacle and said breakable buffer pouch; and
   a cartridge comprising a chamber that comes in fluid communication with said collection reservoir upon docking with said extractor, wherein upon said chamber coming in fluid communication with said collection reservoir, said solution comprising said buffer and said biological sample is subjected to flow from said collection reservoir to said cartridge.

2. The system of claim 1, wherein said sample collector comprises an absorbent-diffuse material that collects, retains, or releases said biological sample.

3. The system of claim 2, wherein said absorbent-diffuse material comprises one or more of a plant fiber material, a disposable material, a flushable material, a biodegradable material, and an organic material.

4. The system of claim 1, wherein said sample collector is insertable in said vaginal canal.

5. The system of claim 1, wherein said sample collector comprises a cup, a rod, a pad, or a threaded matrix.

6. The system of claim 1, wherein said extractor comprises a compression mechanism with a compression unit, wherein said compression unit is movable inwards into said sample receptacle to apply a compression force.

7. The system of claim 6, wherein said compression mechanism comprises a spring, threaded screw, lever, airtight plunger, or manual push syringe that forces said compression element inwards into said sample receptacle in response to activation of said compression mechanism.

8. The system of claim 1, wherein said extractor further comprises a filter disposed between said sample receptacle and said collection reservoir.

9. The system of claim 8, wherein said filter is selected from the group consisting of a cellulose filter, a plastic filter, a metal filter, and any combination thereof.

10. The system of claim 1, further comprising a docking unit that brings said cartridge in fluid communication with said collection reservoir.

11. The system of claim 10, wherein said docking unit comprises a one-way pressure valve or a resealable slit.

12. The system of claim 1, wherein upon said chamber coming in fluid communication with said collection reservoir, said solution comprising said buffer and said biological sample is subjected to flow from said collection reservoir to said cartridge under the influence of a pressure drop.

13. The system of claim 1, wherein said biological sample comprises one or more members selected from the group consisting of cervicovaginal fluid, blood, vaginal mucosa, semen, interstitial fluid, cervical secretions, fetal tissues, reproductive cells, cervical cells, endometrial cells, fallopian cells, ovarian cells, and trophoblast cells.

14. The system of claim 1, wherein said solution comprises a reagent necessary for analyzing said biological sample.

15. The system of claim 1, wherein said solution comprises a reagent necessary for (i) hydrolyzing, diffusing, or releasing said biological sample, (ii) analyzing, preserving or extracting deoxyribonucleic acid, ribonucleic acid or protein in said biological sample, (iii) reducing analysis background noise, (iv) precipitating or removing a contaminant in said biological sample, or (v) testing said biological sample for a presence or absence of an analyte in said biological sample.

16. The system of claim 1, further comprising a container for storing or shipping said cartridge.

17. The system of claim 1, further comprising a cartridge reader for (1) detecting an analyte in said biological sample, and (2) capturing and interpreting a result from said detecting.

18. The system of claim 17, wherein said analyte is for testing a presence or absence of a health condition of said subject selected from the group consisting of sexually transmitted infections, yeast infection, fungal infection, bacterial infection, viral infection, viroid infection, parasite infection, protozoa infection, cancer, pregnancy, fertility, semen, hormone levels, endometriosis, polycystic ovarian syndrome, reproductive disorders, immune disorders, and nutrient levels.

19. A method for extracting and preserving components of a biological sample of a subject in their original state, comprising:
   (a) using a sample collector to non-invasively collect said biological sample from a vaginal canal of said subject, wherein said sample collector collects and retains said biological sample from said vaginal canal;
   (b) bringing said sample collector in proximity to an extractor comprising (i) a sample receptacle configured to receive said sample collector via an opening, (ii) a breakable buffer pouch comprising a buffer for preserving said components of said biological sample in their original state during storage or shipping of said biological sample for subsequent processing or analysis of said biological sample, wherein said breakable buffer pouch is separate from said sample receptacle and configured to release said buffer to contact said sample collector in said sample receptacle when said breakable buffer pouch is broken, and (iii) a collection reservoir that is in fluid communication with each of said sample receptacle and said breakable buffer pouch when said breakable buffer pouch is broken, wherein said collection reservoir is separate from said sample receptacle and said breakable buffer pouch;

(c) depositing said sample collector through said opening into said sample receptacle;

(d) receiving, in said collection reservoir, a solution comprising said buffer from said breakable buffer pouch and said biological sample from said sample receptacle; and (e) docking a cartridge comprising a chamber with said extractor, thereby bringing said chamber in fluid communication with said collection reservoir, wherein upon said chamber coming in fluid communication with said collection reservoir, said solution comprising said buffer and said biological sample is subjected to flow from said collection reservoir to said cartridge.

20. The method of claim 19, wherein said sample collector comprises an absorbent-diffuse material that collects, retains, or releases said biological sample.

21. The method of claim 19, wherein said sample collector is insertable in said vaginal canal.

22. The method of claim 19, wherein said sample collector comprises a cup, a rod, a pad, or a threaded matrix.

23. The method of claim 19, wherein said biological sample comprises one or more members selected from the group consisting of cervicovaginal fluid, blood, vaginal mucosa, semen, interstitial fluid, cervical secretions, fetal tissues, reproductive cells, cervical cells, endometrial cells, fallopian cells, ovarian cells, and trophoblast cells.

24. The method of claim 19, wherein said solution comprises a reagent necessary for analyzing said biological sample.

25. The method of claim 19, further comprising (1) detecting an analyte in said biological sample, and (2) capturing and interpreting a result from said detecting.

26. The method of claim 25, wherein said analyte is for testing a presence or absence of a health condition of said subject selected from the group consisting of sexually transmitted infections, yeast infection, fungal infection, bacterial infection, viral infection, viroid infection, parasite infection, protozoa infection, cancer, pregnancy, fertility, semen, hormone levels, endometriosis, polycystic ovarian syndrome, reproductive disorders, immune disorders, and nutrient levels.

27. The method of claim 19, further comprising sequencing a nucleic acid in said biological sample.

28. The method of claim 19, further comprising storing or shipping said cartridge comprising said solution comprising said biological sample.

29. The system of claim 1, wherein said breakable buffer pouch in said extractor comprises a buffer for diffusing or releasing said biological sample from said sample collector.

* * * * *